US006511971B1

(12) United States Patent
Gorun

(10) Patent No.: US 6,511,971 B1
(45) Date of Patent: Jan. 28, 2003

(54) SUBSTITUTED PERHALOGENATED PHTHALOCYANINES

(75) Inventor: Sergiu M. Gorun, Providence, RI (US)

(73) Assignee: Brown University Research Foundation, Providence, RI (US)

( * ) Notice: Subject to any disclaimer, the term of this patent is extended or adjusted under 35 U.S.C. 154(b) by 0 days.

(21) Appl. No.: 09/416,457

(22) Filed: Oct. 12, 1999

Related U.S. Application Data
(60) Provisional application No. 60/103,987, filed on Oct. 13, 1998.

(51) Int. Cl.[7] ..................... C07D 487/22; A61K 31/409
(52) U.S. Cl. ........................ 514/183; 540/122; 540/136; 540/137; 540/139; 540/140; 514/184; 514/185
(58) Field of Search ................................ 540/122, 136, 540/137, 139, 140; 514/183, 184, 185

(56) References Cited

U.S. PATENT DOCUMENTS

| 4,576,173 A | 3/1986 | Parker et al. ................ 128/633 |
| 4,592,361 A | 6/1986 | Parker et al. ................ 128/633 |
| 4,649,151 A | 3/1987 | Dougherty et al. .......... 514/410 |
| 4,656,186 A | 4/1987 | Bommer et al. ............. 514/410 |
| 4,693,885 A | 9/1987 | Bommer et al. ................. 424/2 |
| 4,814,256 A * | 3/1989 | Aldag et al. ................. 430/270 |
| 4,827,938 A | 5/1989 | Parker ......................... 128/633 |
| 4,861,876 A | 8/1989 | Kessel ......................... 540/145 |
| 4,866,168 A | 9/1989 | Dougherty et al. .......... 540/145 |
| 4,889,129 A | 12/1989 | Dougherty et al. .......... 128/664 |
| 4,913,907 A | 4/1990 | Jori et al. .................... 424/450 |
| 4,932,934 A | 6/1990 | Dougherty et al. ............ 604/21 |
| 5,484,778 A | 1/1996 | Kenney et al. ................ 514/63 |
| 5,945,439 A | 8/1999 | Richter et al. ............... 514/410 |

FOREIGN PATENT DOCUMENTS

| EP | 0 134 518 | 7/1988 |
| EP | 0 155 780 | 3/1990 |
| EP | 0 337 209 | 8/1993 |
| GB | 2229190 | 9/1990 |
| JP | 63141982 A2 * | 6/1988 |
| JP | 02049785 A2 * | 2/1990 |
| JP | 05222046 A2 * | 8/1993 |
| JP | 06072873 A2 * | 3/1994 |

OTHER PUBLICATIONS

Howe et al J. Phys. Chem. A 101 (1997) 3207–3213.*
Nishisaka et al Chemical Abstract accession No. 1994:290090 for JP–06072873.*
Ito et al Chemical Abstract accession No. 1994:314462 for JP–05222046.*
Yamada et al Chemical Abstract accession No. 1990:508094 for JP–02049785.*
Okidaka et al Chemical Abstract accession No. 1989:77513 for JP–63141982.*

Abe, H. et al., "Analysis of Viral DNA, Protein and Envelope Damage After Methylene Blue, Phthalocyanine Derivative or Merocyanine 540 Photosensitiation," *Photochem. Photobiol.* 61(4):402–409 (1995).
Abernathy, C.D. et al., "Activity of Phthalocyanine Photosensitizers against Human Glioblastoma in Vitro," *Neurosurgery*, 21(4):468–473 (1987).
Allémann, E. et al., "Photodyanamic Activities and Biodistribution of Fluorinated Zinc Phthalocyanine Derivatives in the Murine EMT–6 Tumour Model," *Int. J. Cancer*, 72:289–294 (1997).
Allémann, E. et al., "Photodynamic Therapy of Tumours with Hexadecafluoro Zinc Phthalocyanine Formulated in Peg–Coated Poly(Lactic Acid) Nanoparticles," *Int. J. Canc.* 66:821–824 (1996).
Allen C.M. et al., "Sulfophthalocyanines for Photodynamic Inactivation of Viruses in Blood Products: Effect of Structural Modifications," *Photochem. Photobiol.* 62(1):184–189 (1995).

(List continued on next page.)

Primary Examiner—Richard L. Raymond
Assistant Examiner—Kahsay Habte
(74) Attorney, Agent, or Firm—Lahive & Cockfield, LLP; Peter C. Lauro, Esq.

(57) ABSTRACT

Phthalocyanine compounds of the formulas I and II:

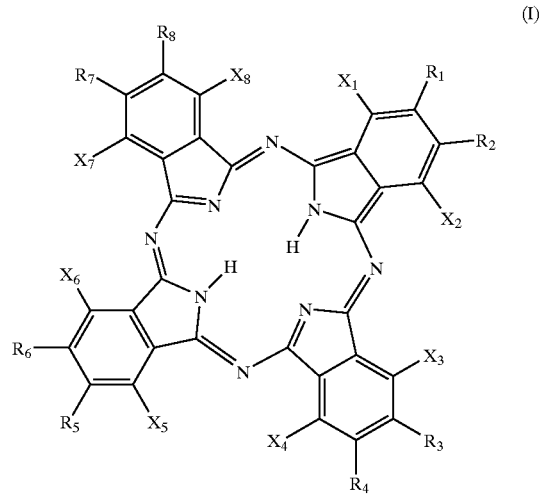

(I)

wherein $X_{1-8}$ are each halogen and $R_{1-8}$ are each independently halogen or an anti-stacking moiety; and

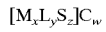

(II)

wherein M is a metal, L is an anion of a phthalocyanine compound of formula I as defined above, S is an organic or inorganic ligand, C is a counterion, x and y are numbers greater than zero, and z and w are numbers zero or greater, are disclosed. Pharmaceutical compositions comprising the compounds and methods of using the compounds, for example for treatment of cancer, are also disclosed.

70 Claims, 3 Drawing Sheets

OTHER PUBLICATIONS

Ben–Hur, E. et al., "The phthalocyanines: a new class of mammalian cells photosensitizers with a potential for cancer phototherapy," *Int. J. Radiat. Biol.* 47(2):145–147 (1985).

Berg, K. et al., "Evaluation of sulfonated aluminum phthalocyanines for use in phtochemotherapy. Cellular uptake studies," *Cancer Letters* 44:7–15 (1989).

Berge, S. M. et al., "Pharmaceutical Salts", *J. Pharm. Sci.* 66(1):1–19 (1977).

Bonnet, Raymond, "Photosensitizers of the Porphyrin and Phthalocyanine Series for Photodynamic Therapy," *Chem. Soc. Rev.* 19:19–33 (1995).

Brasseur, N. et al., "Synthesis and Photodynamic Activities of Silicon 2,3–Naphthalocyanine Derivatives," *J. Med. Chem.* 37:415–420 (1994).

Brédas, J. L. et al., "Third–Order Nonlinear Optical Response in Organic Materials: Theoretical and Experimental Aspects," *Chem. Rev.* 94:243–278 (1994).

Britton, Doyle, "Tetrafluorophthalonitrile," *Acta Crystallogr., Sect C (CrStr. Comm.)* 44:1020–1022 (1988).

Chan, W.S. et al., "Tissue Uptake, Distribution, and Potency of the Photoactivatable Dye Chloroaluminum Sulfonated Phthalosyanine in Mice Bearing Transplantable Tumors," *Cancer Res.* 48:3040–3044 (1988).

Cheradame, Hervé, "A Comprehensive Theory of the High Ionic Conductivity of Macromolecular Networks," *Macromolecules*, ed. Benoit, H. and Rempp, P. (Pergamon Press: New York, 1982), 251–264.

Cotton & Wilkinson, *Advanced Inorganic Chemistry*, (John Wiley & Sons, New York, 1972) p. 626.

Dhami, S. et al., "Comparison of the photophysics of an aggregating and non–aggregating aluminium phthalocyanince system incorporated into unilamellar vesicles," *J. Photochem. Photobiol A: Chem.* 100:77–84 (1996).

Esposito, J. N. et al., "Infrared and Nuclear Magnetic Resonance Studies of Some Germanium Phthalocyanines and Hemiporphyrazines," *Inorg. Chem.* 6(6):1116–1120 (1967).

Gerstenberger, M. R. C. et al., "Methods of Fluorination in Organic Chemistry," *Angew. Chem., Int. Ed. Engl.* 20:647–667 (1981).

Gorun, S. M. et al., "Synthesis and structural characterization of non–planar perfluoro phthalonitriles," *J. Fluorine. Chem.* 91:37–40 (1998).

Guillon, D. et al., "Columnar Mesophases From Metal and Metal–free Derivatives of Phthalocyanine," *Mol. Cryst. Liq. Cryst.*; 130:223–229 (1985).

Howe, L. et al., "Ultrafast Studies of Excited–State Dynamics of Phthalocyanine and Zinc Phthalocyanine Tetrasulfonate in Solution," *J. Phys. Chem. A*, 101:3207–3213 (1997).

Iliev, V. et al., "Oxidation and photooxidation of sulfur–containing compounds in the presence of water soluble phthalocyanine complexes," *Molecular Catalysis A: Chemical* 103:174–153 (1995).

Khan, Frederic J., "ir–laser–addressed thermo–optic smectic liquid–crystal storage displays," *Appl. Phys. Lett.* 22(3):111–113 (1973).

Kimura, Mutsumi et al., "Catalytic Oxidation of 2–Mercaptoethanol by Cationic Water–soluble Phthalocyaninatocobalt(II) Complexes," *J. Porphyrins Phthalocyanines*, 1:309–313 (1997).

Kimura, M. et al., "Dendritic metallophthalocyanines: synthesis and characterization of a zinc(II) phthalocyanine[8] 3–arborol," *Chem. Commun.* 1215–1216 (1997).

Krishnamurti, Ramesh et al., "Preparation of trifluoromethyl and Other Perfluoroalkyl Compounds with (Perfluoroalkyl)trimethylsilanes," *J. Org. Chem.* 56:984–989 (1991).

Lever, A.B.P., "The other periodic chart," *Chemtech*, 17:506–510 (1987).

Margaron, Philippe et al., "Biological Activities of Phthalocyanines, XVII. Histopathologic Evidence for Different Mechanisms of EMT–6 Tumor Necrosis Induced by Photodynamic Therapy with Disulfonated Aluminum Phthalocyanine or Photofrin," *Anticancer Res.* 16:613–620 (1996).

Margaron, Philippe et al., "Structure–Photodynamic Activity Relationships of a Series of 4–Substituted Zinc Phthalocyanines," *Photochem. and Photobiol.* 63(2):217–223 (1996).

Milgrom, Lionel et al., "Light ahead," *Chemistry in Britain*, 45–50 (May 1998).

Piechocki, C and Simon, J., "Annelides XI. Elaboration of Molecular Materials. Synthesis of Octasubstituted Phthaloxyanine Derivatives Forming Discotic Mesophases," *New Journal of Chemistry (Nouveau Journal De Chimie)*, 9(3):159–166 (1985).

Rockwell, Sara C. et al., "Characteristics of a Serially Transplanted Mouse Mammary Tumor and Its Tissue–Culture–Adapted Derivative," *J. Nat. Cancer Inst.*, 49(3):735–749 (1972).

Rosenthal, I. et al., "The Effect of Substituents on Phthalocyanine Photocytotoxicity," *Photochem. Photobiol.* 46(6):959–963 (1987).

Rywkin, S. et al., "New Phthalocyanines for Photodynamic Virus Inactivation in Red Blood Cell Concentrates," *Photochem. Photobiol.* 60(2):165–170 (1994).

Schelly, Z. A. et al., "Bonding in Dye Aggregates. Energetics of the Dimerization of Aqueous Cobalt(II)–4,4',4''',4'''–Tetrasulfophthalocyanine Ion," *J. Phys. Chem.* 74(16):3040–3042 (1970).

Schutte, W. J. et al., "Aggregation of an Octasubstituted Phthalocyanine in Dodecane Solution," *J. Phys. Chem.* 97(22):6069–6073 (1993).

Sonoda, M. et al., "The Role of Singlet Oxygen in the Photohemolysis of Red Blood Cells Sensitized by Phthalocyanine Sulfonates," *Photochem Photobiol.* 46(5):625–631 (1987).

Spikes, John D., "Phthalocyanines as Photosensitizers in Biological Systems and for the Photodynamic Therapy of Tumors," *Photochem. Photobiol.* 43(6):691–699 (1986).

Tada, Hiroko et al., "An improved colorimetric assay for interleukin2," *J. Immunol. Methods*, 93:157–165 (1986).

Tai, Seiji et al., "Strong Aggregation Properties of Novel Naphthalocyanines," *J. Chem. Soc. Perkin Trans. 2*: 1275–1279 (1991).

Vacus, J. et al., "Luminescence and Anti–Aggregatuve Properties of Polyoxyethylene–Substituted Phthalocyanine Complexes," *Adv. Mater.* 7(9):797–800 (1995).

Van Nostrum, Cornelus F. et al., "Construction of a Multi–wired Molecular Cable of Micrometer Length by a Self–Assembly Process," *Angew. Chem. Int. Ed. Eng.*, 33(21):2173–2175 (1994).

Witkiewicz, Z. et al., "Properties of octamethoxyphthalocyanines, I. On their synthesis, electrical conductivity, and catalytic activity," *Materials Science* II, 1–2:39–45 (1976).

Yang, Y.C. et al., "Dimerization of Cobalt(II) Tetrasulfonated Phthalocyanine in Water and Aqueous Alcoholic Solutions," *Inorg. Chem.* 24:1765–1769 (1985).

Butin et al., "Electrochemical potentials and reactivity of organometallic compounds. Dodecachorotetrakis(3,5–di–tert–butyl–4–hydroxyphenyl)phthalocyanine metal complexes," *Chemical Abstract* XP002130434 vol. 113(12) p. 532 (1990).

Griffiths et al., "Some observations on the synthesis of polysubstituted zinc phthalocyanine sensitisers for photodynamic therapy," *Dyes and Pigments*, 33(1):65–78 (1997).

Kolnin et al., "Synthesis of rare earth monophthalocyanines containing fragments of sterically hindered phenols," *Chemical Abstract* XP002130432 vol. 123 (6) p. 1235 (1995).

Kuznetsov et al., "Inhibiting and catalytic properties of metal phthalocyanines during liquid–phase oxidation of styrene," *Chemical Abstract* XP002130433 vol. 124(18) p. 3 (1996).

Milaeva et al., "Tetrakis(3,5–di–tert–butyl–4–hydroxyphenyl)metallophthalocyanines and their free radicals," *Chemical Abstract* XP002130431 vol. 112(20) p. 783 (1990).

Milaeva et al., "ESR study of the interaction of tetrakis (3,5–di–t–butyl–4–hydroxyphenyl)do decachlorophtalocyaniatocobalt (II) with dioxygen," *Inorganica Chimica Acta*, 167(2):139–141 (1990).

Milaeva et al., "Cobalt tetraphenol–substituted phthalocyanine. A spectroscopic study of redox properties in solution," *Inorganica Chinica Acta*, 192(1):117–121 (1992).

\* cited by examiner

SUBSTITUTED PERHALOGENATED PHTHALOCYANINES

RELATED APPLICATIONS

This application claims priority to U.S. Provisional Application, Serial No. 60/103,987 filed on Oct. 13, 1998, entitled "Substituted Perfluorinated Phthalocyanines." The entire contents of the provisional application are incorporated herein by reference.

BACKGROUND OF THE INVENTION

Phthalocyanines are a group of photoactive compounds that are somewhat structurally similar (i.e., have nitrogen containing ring structure) to the porphyrin family. Phthalocyanines are azaporphyrins consisting of four benzoindole nuclei connected by nitrogen bridges in a 16-membered ring of alternating carbon and nitrogen atoms around a central metal atom (i.e., $C_{32}H_{16}N_8M$) which form stable chelates with metal cations. In these compounds, the ring center is occupied by a metal ion (such as a diamagnetic or a paramagnetic ion) that may, depending on the ion, carry one or more ligands. In addition, the ring periphery may be either unsubstituted or substituted.

Owing to their high stability and unique physicochemical properties, phthalocyanines and related macrocycles have found widespread applications in various disciplines (*Phthalocyanines-Properties and Applications*; Leznoff and Lever, Eds.; VCH: New York, 1989, Vol. 1; 1993, Vols. 2 and 3; 1996, Vol. 4.) Numerous studies have been carried out to modify these tetrapyrrole derivatives with the goal of modifying their properties and optimizing their performance as advanced materials. For some applications, such as photodynamic therapy, photoinactivation of viruses in stored blood products, and the photooxidation of mercaptans in petroleum distillates, it is desirable that the macrocycles are free of molecular aggregation (Bonnet, *Chem. Soc. Rev.* 1995, 19; Milgrom et al. *Chem. Br.* 1998 (May), 45; Rywiken, S. et al. *Photochem. Photobiol.* 1994, 60:165; Abe, H. et al. *Photochem. Photobiol.* 1995, 61:402; Allen, C. M. et al. *Photochem. Photobiol.* 1995, 62:184; Iliev, V. et al. *J. Chem. Soc. Catal. A. Chem.* 1995, 103:147; Kimura et al. *J. Porphyrins Phthalocyanines*, 1997, 1:309).

Molecular aggregation, a common phenomenon of this family of compounds, drastically decreases the compounds' luminescence quantum yield, which results in decreased photosensitizing efficiency (Tai, S. et al. *J. Chem. Soc. Perkin Trans.* 2 1991, 1275; Schutte, W. et al. *J. Phys. Chem.* 1993, 97:6069; Spikes, D. J. *Photochem. Photobiol.* 1986, 43:691; Vacus, J. et al *Adv. Mater.* 1995, 7:797; Dharni, S et al. *J. Photochem. Photobiol A: Chem.* 1996, 100:77; Howe, L. et al. *J Phys. Chem.* A, 1997, 101:3207). Increased water solubility of phthalocyanines has been shown to decrease their aggregation tendencies (Schelly, Z. A. et al. *J. Phys. Chem.* 1970, 74:3040; Yang, Y. C. et al. *Inorg. Chem.* 1985, 24:1765). Hydrophilic and non-aggregating phthalocyanines are potentially useful materials, but the study of these phthalocyanines is still in its infancy (Kimura, M. et al. *Chem. Commun.* 1997, 1215).

SUMMARY OF THE INVENTION

The invention pertains, at least in part, to phthalocyanine compounds of formula

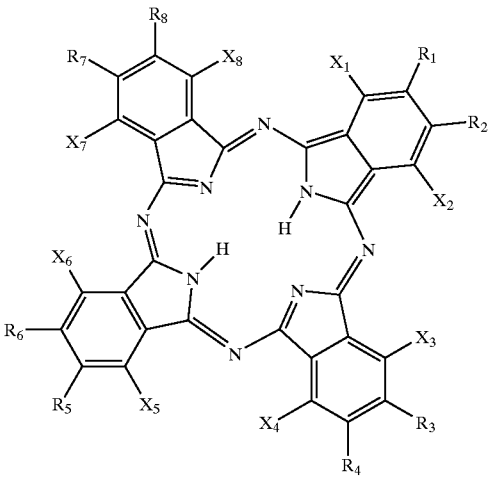

(I)

wherein $X_{1-8}$ are each halogen and $R_{1-8}$ are each independently halogen or an anti-stacking moiety.

The invention also includes phthalocyanine compounds of formula II:

$$[M_xL_yS_z]C_w \qquad (II)$$

wherein M is a metal, L is an anion of a phthalocyanine compound of formula I as defined above, S is an organic or inorganic ligand, C is a counterion, x and y are numbers greater than zero, and z and w are numbers zero or greater. In preferred embodiments, M is a metal cation.

In one embodiment, $R_{1-8}$ are not all halogen. In another embodiment, each of $X_{1-8}$ is fluorine. In another embodiment, the anti-stacking moieties are inert to activated oxygen and may be selected such that the phthalocyanine compound is soluble in water. In yet another embodiment, the anti-stacking moieties are branched alkyl and are, advantageously, perhalogenated. In one embodiment, the anti-stacking moiety is perfluorinated branched alkyl. In another embodiment, M is diamagnetic.

The invention also pertains to a pharmaceutical composition, comprising a pharmaceutically acceptable carrier and an effective amount of a phthalocyanine compound of formula II, as described above, and pharmaceutically acceptable salts thereof. In one embodiment, the pharmaceutical composition is suitable for the treatment of a condition in a patient. In a preferred embodiment, the composition is suitable for treating cancer in a patient, e.g., by using photodynamic therapy.

In yet another embodiment, the invention features a method for treating a condition in a patient, by administering to the patient an effective amount of a phthalocyanine compound of formula II, as described above. In one embodiment, the method comprises exposing the patient to light to achieve photodynamic therapy. Preferably, the condition is cancer and the effective amount is effective to treat cancer.

The invention also includes a method of photoinactivating viruses in blood, by contacting the blood with an effective amount of a phthalocyanine compound of formula II, as described above. The invention also pertains to a dye and a composition for organometallic catalysis each comprising at least one phthalocyanine compound of formula II.

BRIEF DESCRIPTION OF THE DRAWINGS

In the following figures, nitrogen atoms (N) are represented by open circles, carbon atoms (C) are represented by hashed circles, and fluorine atoms are represented by dotted circles.

DETAILED DESCRIPTION OF THE INVENTION

Figure 1:
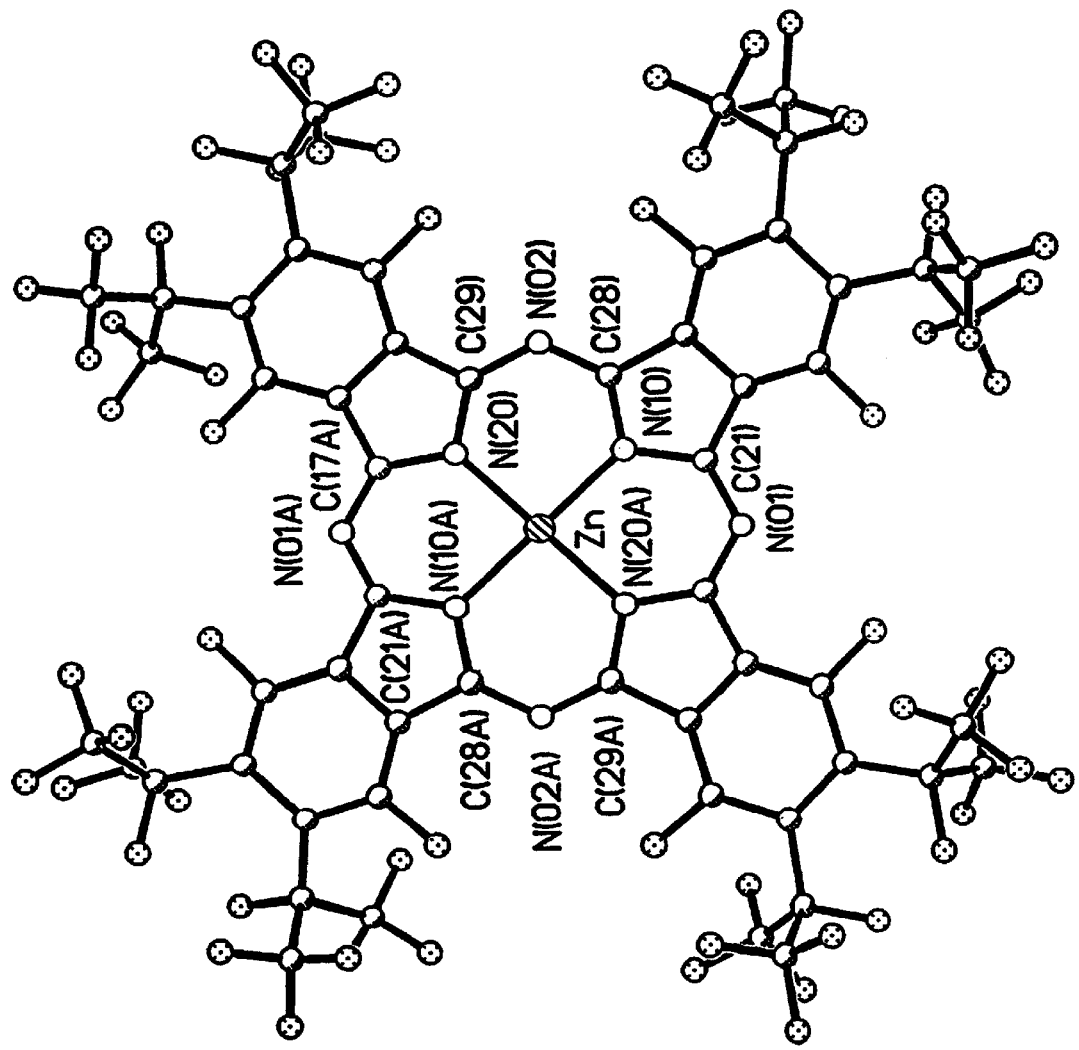
FIG. 1 is a perspective view of the single crystal X-ray structure of zinc octakis (perfluoroisopropyl) perfluorophthalocyanine bis-acetone, shown without the two acetone ligands for the sake of clarity.

Phthalocyanines are widely used organic molecules that are capable of binding ions forming metallophthalocyanines. Both phthalocyanines and metallophthalocyanines have widespread uses ranging from electronic materials and catalysis to photodynamic cancer therapy. The invention pertains to phthalocyanine compounds and methods of their use.

Phthalocyanines were among the earliest classes of synthetic macrocyclic tetraamines to be discovered (Cotton & Wilkinson, *Advanced Inorganic Chemistry*, (John Wiley & Sons, New York, 1972) p. 626). One method of preparing phthalocyanines is the annexed type reaction, shown below in Scheme 1, in which the metal ion plays an essential role as a template. Similar methods of preparing phthalocyanines involve the use of metals of other oxidation states. Phthalocyanines characteristically have exceptional thermal stability, subliming in a vacuum at temperatures around 500° C.; they are an important commercial class of pigments. Their conjugated π system gives a pronounced ring current, which can be exploited in studying NMR spectra (Esposito, J. N. et al. *Inorg Chem.* 1967, 6:1116).

Scheme 1

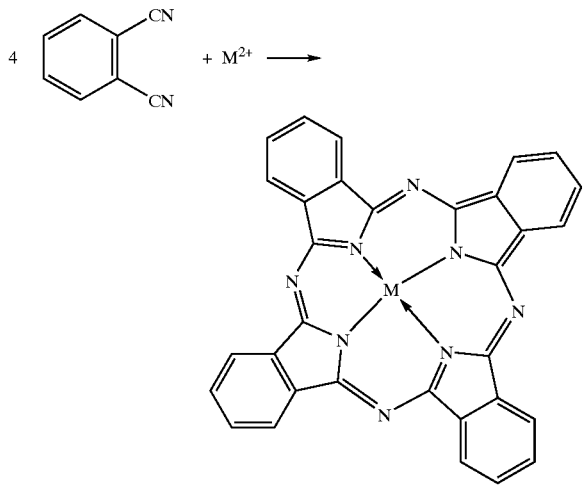

The synthesis of compounds of the invention is discussed in detail in Examples 1–6.

1. Definitions

Before further description of the invention, certain terms employed in the specification, examples and appended claims are, for convenience, collected here.

The language "activated oxygen" or "singlet oxygen" refers to excited molecular oxygen. The lowest-energy electron configuration of the $O_2$ molecule contains two electrons in $\pi^*$ orbitals, which give rise to three possible electron configurations: one is triplet (ground state oxygen) and the other two are singlet (excited states). Oxygen molecules in excited singlet states, especially the $^1\Delta_g$ state, react with a variety of unsaturated organic substrates to cause limited, specific oxidations. For example, activated oxygen can react in a Diels-Alder type 1,4-addition with 1,3-diene to form a dioxane. In general, there are at least three ways of generating activated oxygen. First, it can be produced from triplet oxygen by irradiation in the presence of a sensitizer (e.g., compounds of the invention). It also can be produced chemically and through electrodeless discharge. Not wishing to be bound by theory, it is thought that the sensitizer (e.g., compounds of the invention) absorb the irradiation and then transfer the energy to unactivated, triplet oxygen to form ultimately activated, singlet oxygen.

The term "alkenyl" includes unsaturated aliphatic groups analogous in length and possible substitution to the alkyls described below, but that contain at least one double bond. Unless the number of carbons is otherwise specified, "lower alkenyl" refers to an alkenyl group, as defined above, but having from two to four carbon atoms in its backbone structure.

The term "alkyl" includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term alkyl further includes alkyl groups, which can further include heteroatoms replacing one or more carbons of the hydrocarbon backbone, e.g., oxygen, nitrogen, sulfur or phosphorous atoms. In one embodiment, a straight chain or branched chain alkyl has 20 or fewer carbon atoms in its backbone (e.g., $C_1$–$C_{12}$ for straight chain, $C_3$–$C_{12}$ for branched chain). Examples of alkyl groups contemplated by the invention include, but are not limited to, methyl, ethyl, isopropyl, isobutyl, tert-butyl, branched pentyl, branched hexyl, cyclohexyl, and cyclopentyl groups.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyll phosphate, phosphonato, phosphinato, cyano, amino (including alkyl amino, dialkylamino, arylamino, diarylamino, and alkylarylamino), arylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)). Unless the number of carbons is otherwise specified, "lower alkyl" refers to an alkyl group, as defined above, but having from one to three carbon atoms in its backbone structure. The terms "alkoxyalkyl", "polyaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkynyl" includes unsaturated aliphatic groups analogous in length and possible substitution to the alkyls described above, but that contain at least one triple bond. Unless the number of carbons is otherwise specified, "lower alkynyl" refers to an alkynyl group, as defined above, but having from two to four carbon atoms in its backbone structure.

The term "anti-stacking moiety" includes substituents which enhance the ability of the phthalocyanine to perform its intended function, e.g., act as a photodynamic cancer therapeutic agent, a dye, etc. The anti-stacking moieties in accordance with the invention discourage molecular aggregation or "stacking" of the phthalocyanines by making the phthalocyanine non-planar. In an embodiment of the invention, the anti-stacking moiety is selected such that the distance between adjacent molecular planes of phthalocyanine compounds is at least about 3 Å, preferably about 4 Å. The term "anti-stacking moiety" also includes moieties which enhance the phthalocynanine's solubility, luminescence quantum yield, or otherwise enhance its ability to perform its intended function. Examples of "anti-stacking moieties" include alkyl, alkenyl, alkynyl, aryl, heteroaryl, and aralkyl moieties. Anti-stacking moieties may be $C_1$–$C_{20}$, preferably $C_3$–$C_{12}$, and more preferably $C_3$–$C_6$. Advantageously, anti-stacking moieties are branched or otherwise sterically bulky (e.g., isopropyl, isobutyl, tertbutyl, or branched pentyl) and may be perhalogenated, e.g., perfluorinated. Furthermore, preferred anti-stacking moieties are inert to activated oxygen.

The term "aryl" includes aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin). The term "aralkyl" includes alkyl groups substituted with at least one aryl group and aryl groups substituted with at least one alkyl group.

The term "diamagnetic metal atom" includes metal atoms and ions with no unpaired electrons.

The term "heteroatom" as used herein means an atom of any element other than carbon or hydrogen. Preferred heteroatoms are nitrogen, oxygen, sulfur and phosphorus.

The language "inert to activated oxygen" includes moieties and compounds which do not readily react with activated or singlet oxygen. Examples of moieties which are inert to activated oxygen include, for example, perhalogenated alkyl groups, and in certain embodiments of the invention, perfluorinated alkyl groups.

The term "metal" is used in its broadest sense and includes metal and metalloid atoms and ionic species derived therefrom, e.g., cations, which can interact with and form a complex with an anion of a phthalocyanine compound of the invention. The term "metal" also includes ground state species.

The term "metalloids" includes elements which have properties intermediate between those of metals and non-metals. Examples of metalloids include B, Si, Ge, As, Sb, Te, Po and At.

The term "paramagnetic metal atom" includes metal atoms and ions with unpaired electrons.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The term "perfluorinated" includes alkyl, alkenyl, alkynyl, aryl, etc. moieties which are substituted completely with fluorine atoms and contain no hydrogen atoms.

The term "perhalogenated" includes alkyl, alkenyl, alkynyl, aryl, etc. moieties which are substituted completely with halogen atoms and contain no hydrogen atoms.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as[]glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. Hydroxyls can be converted into esters via treatment with an esterifying agent such as alkanoyl halides. The term also includes lower hydrocarbon groups capable of being solvated under physiological conditions, e.g., alkyl esters, methyl, ethyl and propyl esters. (See, for example, Berge et al., supra.)

The term "pharmaceutically acceptable salts" is art recognized and includes relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1–19).

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The term "photodynamic therapy" or "PDT" refers to a process for treating a condition in a subject, e.g., cancer, where visible light is used to activate a photodynamic sensitizer, such as a dye or drug. The sensitizers are selectively retained by the cancerous tissue and eliminated by the healthy tissue. The photodynamic sensitizer can be activated by exposure to therapeutic light of an appropriate wavelength and intensity for activation. The light can be directly applied through the skin to the cancerous area from a conventional light source (e.g., laser, sun lamp, or white light sources with appropriate filters), or in cases where the cancerous tissue is located deeper within the body, through surgical or non-surgical entry such as by the use of fiber optic illumination systems such as flexible fiber optic catheters or endoscopic devices. When the photodynamic sensitizer is activated, it reacts photochemically with tumor tissue, producing a cell killing, or cytotoxic, effect.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

2. Compounds

The invention pertains, at least in part, to phthalocyanine compounds represented by formula (I) below:

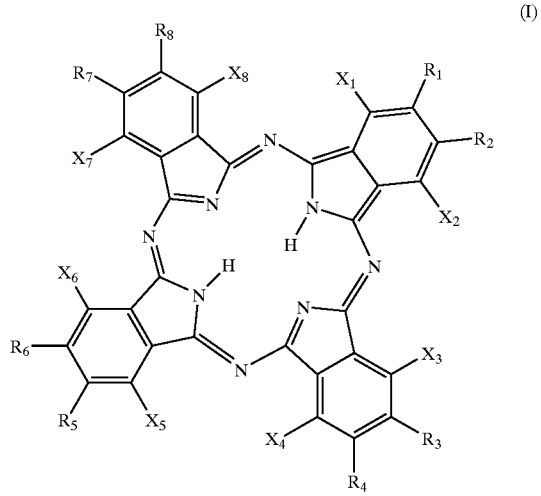

(I)

wherein $X_{1-8}$ are each halogen and $R_{1-8}$ are each halogen or an anti-stacking moiety, provided that $R_{1-8}$ are not each halogen atoms.

The invention also pertains to phthalocyanine compounds of formula II:

$$[M_xL_yS_z]C_w \qquad (II)$$

wherein M is a metal, L is an anion of a phthalocyanine compound of formula I as defined above, S is an organic or inorganic ligand, C is a counterion, x and y are numbers greater than zero, and z and w are numbers zero or greater. In one embodiment, M is a metal cation.

In another embodiment, if $X_{1-8}$ are each chlorine, and $R_2$, $R_4$, $R_6$, and $R_8$, are each unsubstituted methyl, then M is not Co or Y. In another embodiment, if $X_{1-8}$ are each chlorine, and $R_2$, $R_4$, $R_6$, and $R_8$ are each unsubstituted t-butyl, then M is not Co.

In yet another embodiment, if $X_{1-8}$ are each chlorine, then $R_2$, $R_4$, $R_6$, and $R_8$ are not all unsubstituted t-butyl or unsubstituted methyl.

The substitution of fluorine for hydrogen in phthalocyanines may impart enhanced thermal stability, lipophilicity and chemical inertness, because of the 'isogeometric' replacement of C—H by strong C—F bonds (107 kcal/mol). Therefore, in another embodiment, at least one of $X_{1-8}$ is a fluorine atom. Preferably, each of $X_{1-8}$ is a fluorine atom.

In one embodiment, the anti-stacking moiety is alkyl, alkenyl, alkynyl, aryl, arylalkyl or heteroaryl. Preferably, the anti-stacking moiety is inert to activated oxygen and it may be selected such that the compound is soluble in water. Advantageously, the anti-stacking moiety is halogenated. For example, the anti-stacking moiety may be substituted with at least one halogen atom, e.g., a fluorine atom and, in a particularly preferred embodiment, may be perhalogenated, e.g., perfluorinated.

In another embodiment, the anti-stacking moiety is perhalogenated alkyl, e.g, perfluorinated alkyl. In certain embodiments, the perfluorinated alkyl is methyl, ethyl, isopropyl, isobutyl, tertbutyl or pentyl. In other embodiments, the anti-stacking moiety is perfluorinated isopropyl.

In yet another embodiment, the phthalocyanine compound includes one or more anti-stacking moieties. Preferably, each of $R_1$–$R_8$ is an anti-stacking moiety, such as, for example, perfluorinated alkyl, e.g., perfluoroisopropyl.

In the compound of formula II, possible metals include any metal species which is capable of forming a complex with a phthalocyanine. Preferred metal atoms include transition metal atoms, metalloid atoms, lanthanide series metal atoms, actinide series metal atoms, and ions thereof. Diamagnetic metal atoms are particularly advantageous. Examples of metal atoms include Li, Be, B, Na, Mg, Al, Si, P, K, Ca, Sc, Ti, V, Cr, Mn, Fe, Co, Ni, Cu, Zn, Ga, Ge, As, Se and their respective ions. Other metal atoms include Rb, Sr, Y, Zr, Nb, Mo, Tc, Ru, Rh, Pd, Ag, Cd, In, Sn, Sb, Te and their respective ions. Still, other metal atoms include Cs, Ba, U, La, Hf, Ta, W, Re, Os, Ir, Pt, Au, Hg, Tl, Pb, Bi, and Po, and their respective ions. Particularly preferred metal atoms include Al, Si, Mn, Fe, Co, Zn, Ru, and Cd and their respective ions.

Advantageously, the values of x, y, z, and w are selected such that the compound is electrically neutral. The minimum values for x and y are greater than zero, while the minimum values for z and w can be zero. In some embodiments, counterions and coordination by an organic or inorganic ligand are not necessary for the stability or the electric neutrality of the phthalocyanine compound. In yet other embodiments, the values of x, y, z, and w may not be integers.

In one embodiment, M is Zn (II), L is octakis (perfluoroisopropyl) perfluorophthalocyanine, S is acetone, C is not present, x and y are each one, z is two and w is zero.

In another embodiment, M is Ru, L is octakis (perfluoroisopropyl) perfluorophthalocyanine, S is carbon monoxide, C is not present, x, y and z are each one, and w is zero.

In another embodiment, M is Ru, L is octakis (perfluoroisopropyl) perfluorophthalocyanine, S is pyridine, C is not present, x and y are each one, z is two and w is zero.

In yet another embodiment, M is Mn (II), L is octakis (perfluoroisopropyl) perfluorophthalocyanine, C is not present, x and y are each one, z and w are each zero.

In yet another embodiment, M is Co (II), L is octakis (perfluoroisopropyl) perfluorophthalocyanine, S is methanol, C is not present, x and y are each one, z is two and w is zero.

In still another embodiment, M is Fe (II), L is octakis (perfluoroisopropyl) perfluorophthalocyanine, C is not present, x and y are each one, z and w are each zero.

In one embodiment, the phthalocyanine compound comprises at least one counterion, advantageously selected such that the resulting compound is electrically neutral. Examples of anionic counterions include: $F^-$, $Br^-$, $Cl^-$, $I^-$, $NO_3^-$, $BF_4^-$, $OH^-$, $PF_6^-$, $SO_4^{2-}$, $ClO_4^-$, $CO_2H^-$, $SO_3H^-$, and carbon based anions, such as fullerenes. Examples of cationic counterions are $PR_4^+$, $NR_4^+$, and $AsR_4^+$, wherein R is hydrogen, alkyl or aryl. Other organic and organometallic cations are also contemplated.

The organic or inorganic ligands may or may not be bound or associated with the compound. Examples of organic ligands which may coordinate with the phthalocyanine compounds of the invention include acetone, pyridine, methanol, DMF, THF, water, ethanol, propanol, hydrocarbons, halogenated hydrocarbons, and other common organic solvents. Inorganic ligands include, for example, CO, $CO_2$ and $SO_2$.

Preferred phthalocyanine compounds of the invention include, for example, manganese octakis (perfluoroisopropyl) perfluorophthalocyanine and cobalt octakis(perfluoroisopropyl) perfluorophthalocyanine. Particularly preferred compounds include zinc octakis (perfluoroisopropyl) perfluorophthalocyanine, ruthenium octakis(perfluoroisopropyl) perfluorophthalocyanine, and iron octakis(perfluoroisopropyl) perfluorophthalocyanine.

It will be noted that the structure of some of the compounds of this invention include asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by methods known to the skilled artisan.

3. Therapeutic uses and Methods

Since E. Ben-Hur and I. Rosenthal disclosed the potential use of phthalocyanines as photosensitizers in 1985 (E. Ben-Hur and I. Rosenthal, *Int. J. Radiat. Biol.* 47, 145–147, 1985), a great deal of research has produced a number of phthalocyanines for photodynamic therapy. However, the compounds of the invention have improved characteristics over those of previous phthalocyanines.

For example, unlike some of the porphyrin compounds, phthalocyanines strongly absorb clinically useful red light with absorption peaks falling between about 600 and 810 nm (Abernathy, C. D. el al, *Neurosurgery*, 21(4):468–473 (1987)). Red light is normally used for photodynamic therapy because of the increased transparency of biological tissues at longer wavelengths, despite the poor absorption of red light by porphyrins. Thus, the greater absorption of red light by the phthalocyanines over porphyrins indicates deeper potential penetration with the phthalocyanines in photodynamic treatment processes.

In addition, the phthalocyanines offer many benefits over the porphyrin components as photosensitizers in that the phthalocyanines are relatively easy to synthesize, purify, and characterize in contrast to the porphyrins, which are often difficult to prepare. Similarly, the metal phthalocyanines are exceptionally stable compounds in comparison to the porphyrin or porphyrin-like compounds (U.S. Pat. No. 5,484,778).

Furthermore, it has been found that the addition of certain metal cations (e.g., diamagnetic metal cations such as aluminum) to the phthalocyanine ring will, in some instances, create a fairly stable chelate with enhanced photosensitizing tumoricidal activity. While the mechanisms for producing the photoreactions are not entirely clear, the choice of the metal cation is important in that certain metals (e.g., paramagnetic metals) may actually inhibit the phototoxic properties of the resulting compound.

However, only a few of the many possible types of ring-substituted phthalocyanines belonging to this group have been examined. By far the most attention has been given to sulfonated phthalocyanines and to phthalocyanines with peripheral substituents carrying hydroxy, alkoxy, and amino substituents.

The limited variety of phthalocyanines which have been tested vary greatly in their photosensitizing activity. Not wishing to be bound by theory, metal-free phthalocyanines show poor photodynamic activity as do phthalocyanines containing paramagnetic metals. In contrast, those containing diamagnetic metals, such as Al, Sn, and Zn, are active as a result of the long half-life of the triplet state (Abernathy, C. D. et al. *Neurosurgery* 21:468–473, 1987; Chan, W. S. et al. *Cancer Res* 48:3040–3044, 1988; Sonoda, M. et al., *Photochem Photobiol*. 46:625–632, 1987). While in general there appears to be an increase in photosensitizing ability with lipophilicity, some highly lipophilic derivatives, such as a tetraneopentoxy derivative, are poor photosensitizers (Berg, K. et al. *Cancer Letters* 44:7–15, 1989; Rosenthal, I. et al. *Photochem. Photobiol.* 46:959–963, 1987).

The mechanisms by which the photodynamic sensitizer produce their cytotoxic effect on the host cells upon illumination by an appropriate light source are not precisely defined and are the subject of continuing research. Not wishing to be bound by theory, it is thought that there are at least two general mechanisms by which the photodynamic sensitizer absorbs and releases energy. The first general reaction mechanism involves energy transfer from the excited photodynamic sensitizer to oxygen present in the cancerous tissue. The excited photodynamic sensitizer transfers its additional energy to the oxygen, producing singlet molecular oxygen ($^1O_2$) which consequentially alters essential cell components of the surrounding tumor tissue.

More particularly, in the first general reaction mechanism, it is thought that the light energy causes the photodynamic sensitizer to become excited from the ground state, $S_0$, to the first excited singlet state, $S_1$. The photodynamic sensitizer's excited singlet state, $S_1$, is then transformed by intramolecular coupling to the lowest lying triplet state $T_1$. Through a direct intermolecular process discussed in U.S. Pat. Nos. 4,576,173, 4,592,361, and 4,827,938, the photodynamic sensitizer transfers this energy to oxygen molecules present in the tissue and raises them from the ground triplet to the first excited electronic singlet state $^1O_2$. The singlet molecular oxygen, $^1O_2$, destroys or alters vital cellular components such as the cell membrane, etc. ultimately inducing necrosis and destroying the cancerous tissue.

The process by which biological damage occurs as a result of the optical excitation of a photodynamic sensitizer in the presence of oxygen is generally referred to as "photodynamic action". A more detailed discussion concerning the use of photodynamic action in the treatment of cancer is discussed in U.S. Pat. Nos. 4,649,151, 4,866,168, 4,889,129, and 4,932,934, concerning improved hematoporphyrin and porphyrin derivatives for photodynamic therapy.

The second general mechanism thought to be involved in the killing effect produced by certain photodynamic sensitizer involves the production of free radicals. Subsequent reactions of the radicals with organic molecules and/or with oxygen results in the biochemical destruction of the diseased tissue.

Although the exact effective mechanisms of the photochemical reactions which produce death of the cancer cells is not clearly understood and varies depending upon the type of photodynamic sensitizer utilized, what is clear is that photodynamic therapy is effective for the preferential destruction of cancerous tissue. Furthermore, photodynamic therapy has several attractive features over conventional methods for treating cancer such as chemotherapy, radiation, surgical procedures, etc., in that the photodynamic sensitizers used are generally non-toxic, concentrate or remain preferentially in cancer cells, and can be used with other modes of treatment because PDT, generally, does not interfere with other chemicals or processes.

As a result, photodynamic therapy is now used for the treatment of malignant diseases in humans and animals (see, U.S. Pat. No. 5,945,439). For example, photodynamic therapy has been used successfully for the treatment of a broad range of cancers including metastatic breast tumors, endometrial carcinomas, bladder tumors, malignant melanoma, Kaposi's sarcoma, basal cell carcinoma, chondrosarcoma, squamous cell carcinoma, prostate carcinoma, laryngeal papillomas, mycosis fungoides, superficial cancer of the tracheobronchial tree, cutaneous/mucosal papilloma, gastric cancer, enteric cancer, etc.

Currently, porphyrins and porphyrin-like compounds such as chlorins (see U.S. Pat. No. 4,656,186, 4,693,885, and 4,861,876) and enlarged porphyrins, naphthalocyanines, phthalocyanines, platyrins, porphycenes (see U.S. Pat. No. 4,649,151 and 4,913,907), purpurins, texaphyrins, and verdins have been investigated as photosensitizers. Numerous other substances, such as "merocyanine 540", xanthenes (Rhodamine 123 6 G&B) cationic cyanic dyes, chalcogenapyryllium dyes, phenothiazinium derivatives, tetracycline, berbine sulphate, acridine orange, and fluorescein have also been used as photodynamic sensitizers, however, the porphyrin derivatives are generally preferred because they absorb in the long wave length region (red region) of the visible spectrum.

Although many of the above identified substances have demonstrated positive effects in photodynamic therapy, these substances also produce various side effects which limit their use for photodynamic therapy. The most predominant side effect exhibited by many of the currently used substances is the development of uncontrolled photosensitivity reactions in patients after the systemic administration of the photosensitizer and the exposure of the patient to normal sunlight. In this regard, on exposure to the sun, the photodynamic therapy patients can develop generalized skin photosensitization. As a result, the patient, after receiving systemic injections of a photosensitizing substance, is required to avoid bright light, especially sunlight for periods of about four to eight weeks.

Furthermore, because many of the above photosensitizers bind to other non-cancerous cells, some healthy cell destruction can also occur. Similarly, although many of the photosensitizers are soluble in water, large dosages are required for cellular uptake and/or treatment. Thus, use of many of the above indicated photosensitizers is normally limited to patients with severe cancerous tumors and continuing research is being conducted in order to produce photosensitizing substances, and/or methods of administering such substances, that avoid these side reactions as well as produce enhanced photosensitizing effects.

Thus in one aspect, the invention pertains to a pharmaceutical composition, comprising a pharmaceutically acceptable carrier and an effective amount of a phthalocyanine compound of formula II:

$$[M_xL_yS_z]C_w \qquad (II)$$

wherein M is a metal, L is an anion of a phthalocyanine compound of formula I as defined above, S is an organic or inorganic ligand, C is a counterion, x and y are numbers greater than zero, and z and w are numbers zero or greater, and L is an anion of a phthalocyanine compound of formula I as defined above, and pharmaceutically acceptable salts thereof. In one embodiment, the effective amount is effective for photodynamic therapy, e.g., effective for treatment of cancer.

In another aspect, the invention pertains to methods of treating a patient, e.g., for cancer, by administering an effective amount of a phthalocyanine compound of formula II. In one embodiment, the method further comprises exposing the patient to light, e.g., light of 650–700 nm, to achieve photodynamic therapy.

The compounds of the present invention have several advantages over other compounds previously discussed. For example, the present compounds have increased solubility in solvent systems useful for PDT. They absorb light at longer wavelengths which is also advantageous for PDT. Furthermore, the anti-stacking moieties of compounds of the present invention help to prevent molecular aggregation. The reduction in molecular aggregation increases the ability of the compounds to perform their intended function at lower concentrations. The absence of C—H bonds in certain compounds of the present invention decreases the likelihood of activated oxygen reacting with the phthalocyanine compound. Furthermore, the reduction of the number of aromatic halogens susceptible to chemical reactions increases the chemical stability of the compounds.

In addition, as the structure of zinc octakis (perfluoroisopropyl) perfluorophthalocyanine ($ZnPcF_{64}$) demonstrates, the methodology discussed in Examples 1–6 results in the advantageous production of pure single isomers.

Pharmaceutical compositions comprising compounds of the invention may contain wetting agents, emulsifiers and lubricants, such as sodium lauryl sulfate and magnesium stearate, as well as coloring agents, release agents, coating agents, sweetening, flavoring and perfuming agents, and preservatives.

Formulations of the present invention include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxyprop lmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert dilutents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agaragar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes.or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable dose of a compound of the invention will be that amount of the compound which is the lowest dose effective to produce a therapeutic effect; i.e., treat a condition in a subject, e.g., cancer. Such an effective dose will generally depend upon the factors described above. Generally, intravenous and subcutaneous doses of the compounds of this invention for a patient, will range from about 0.0001 to about 100 mg per kilogram of body weight, more preferably from about 0.01 to about 10 mg per kg, and still more preferably from about 0.10 to about 4 mg per kg. If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

As set out above, certain embodiments of the present compounds can contain a basic functional group, such as amino or alkylamino, and are, thus, capable of forming pharmaceutically acceptable salts with pharmaceutically acceptable acids.

In other cases, the compounds of the present invention may contain one or more acidic functional groups and, thus, are capable of forming pharmaceutically acceptable salts with pharmaceutically acceptable bases.

In one embodiment, the pharmaceutical compositions of the present invention may contain one or more of the following compounds: zinc octakis(perfluoroisopropyl) perfluorophthalocyanine, ruthenium octakis (perfluoroisopropyl) perfluorophthalocyanine, manganese octakis(perfluoroisopropyl) perfluorophthalocyanine, or cobalt octakis(perfluoroisopropyl) perfluorophthalocyanine.

In another aspect, the invention pertains to a method of photoinactivating viruses in blood. The method includes contacting the blood with an effective amount of a phthalocyanine compound, such that viruses present in said blood are inactivated. The phthalocyanine compound is of formula II:

$$[M_xL_yS_z]C_w \qquad (II)$$

wherein M is a metal, L is an anion of a phthalocyanine compound of formula I as defined above, S is an organic or inorganic ligand, C is a counterion, x and y are numbers greater than zero, and z and w are numbers zero or greater, and pharmaceutically acceptable salts thereof. In one embodiment, the blood is a stored blood product.

4. Electronic and Industrial uses of Phthalocyanines

Phthalocyanines also have electronic and industrial uses. Thus, in another aspect, the invention pertains to a dye containing at least one phthalocyanine compound of formula II:

$$[(M_x)L_yS_z]C_w \qquad (II)$$

wherein M is a metal, L is an anion of a phthalocyanine compound of formula I as defined above, S is an organic or inorganic ligand, C is a counterion, x and y are numbers greater than zero, and z and w are numbers zero or greater, and acceptable salts thereof.

In another aspect, the invention features a composition for organometallic catalysis. The composition contains at least one phthalocyanine compound of formula II, as described above. In an advantageous embodiment, the phthalocyanine compound is soluble in liquid $CO_2$.

Phthalocyanine compounds are also known to exhibit liquid crystalline behavior. The majority of known liquid crystalline compounds have a "rod-shaped" molecular structure and are often characterized by nematic and/or smectic mesophases. In addition, liquid crystalline compounds with "disc-like" molecular structures are also known. These compounds are termed "discotic" compounds, which can be characterized by discotic nematic or columnar mesophase (s).

Discotic compounds can be based on a number of "cores", e.g. benzene, truxene, metallophthalocyanine, phthalocyanines and triphenylene.

Columnar mesophases, derived from metallated and metal free derivatives of phthalocyanine, have also been developed (Guillon et al *Mol. Cryst. Liq. Cryst.*; 1985, 130:223–229). The synthesis of octa-substituted phthalocyanine derivatives forming discotic mesophases have been reported (Piechocki and Simon, *New Journal of Chemistry*, 1985, 9:3:159–166).

Most liquid crystal compounds are known as thermotropic liquid crystal compounds. Thermotropic liquid crystals exist in dependence of the temperature in certain temperature intervals. For a review of phthalocyanine thermotropics, see Simon and Bassoul in *Phthalocyanines, Properties and Applications*, Ed., C. C. Leznoff and A.B.P. Lever, V.C.H. Publishers 1992, p227.

Some phthalocyanines also absorb radiation in the far-red to near infra-red regions of the electromagnetic spectrum. Compounds which absorb strongly at wavelengths of laser light can in principle be exploited as guest dyes dissolved in liquid crystalline host materials in a laser addressed system.

Materials have been proposed for laser addressed applications in which laser beams are used to scan across the surface of the material or leave a written impression thereon. For various reasons, many of these materials have consisted of organic materials which are at least partially transparent in the visible region. The technique relies upon localized absorption of laser energy which causes localized heating and in turn alters the optical properties of the otherwise transparent material in the region of contact with the laser beam. Thus as the beam traverses the material a written impression of its path is left behind. One of the most important of these applications is in laser addressed optical storage devices, and in laser addressed projection displays in which light is directed through a cell containing the material (such as smectic liquid crystal material) and is projected onto a screen (Khan, *Appl. Phys. Lett*. 1973, 22:111) Devices which use a liquid crystal material as the optical storage medium are an important class of such devices. The use of semiconductor lasers, especially $Ga_x, Al_{1-31}$ As lasers where x is from 0 to 1, and is preferably 1, has proven popular in the above applications because they can provide laser energy at a range of wavelengths in the near infra-red which cannot be seen and thus cannot interfere with the visual display, and yet can provide a useful source of well-defined, intense heat energy. Gallium arsenide lasers provide laser light at wavelengths of about 850 nm, and are useful for the above applications. With increasing Al content (x<1), the laser wavelength may be reduced down to about 750 nm.

One of the main problems associated with the use of the above materials is that it has proved difficult to provide materials which are transparent in the visible region and yet are strong absorbers in either the UV or IR region, preferably in the near-IR region. The use of dyes within these materials can provide strong absorption at certain wavelengths, but few dyes are transparent in the visible region and many are insoluble in the type of materials used for laser addressed applications. EP-A-0155780 discloses a group of metal and metal-free phthalocyanines which have been used as infra-red absorbing dyes for a number of applications. These phthalocyanines contain from 5 to 16 peripheral organic substituent groups that are linked to the phthalocyanine through sulphur, selenium, tellurium or nitrogen atoms. However, very few of the groups disclosed absorb infra-red radiation strongly at or near the wavelength of a gallium arsenide laser (850 nm). This problem also applies to a further group of infra-red absorbing phthalocyanines disclosed in EP-A-0134518. This further group consists of naphthalocyanines which are peripherally substituted with alkyl groups and centrally substituted with a metal atom or a chloride, bromide or oxide thereof. The synthesis of octamethoxyphthalocyanines is disclosed but these compounds are insoluble in organic solvents and insoluble compounds are unsuitable for acting as dyes in liquid crystalline solvents for laser addressed systems (*Materials Science II*, 1976 1–2:39–45).

UK Patent GB 2,229,190 B relates to certain substituted phthalocyanines, methods for their preparation and to certain uses thereof. For example, the compounds described in GB 2,229,190 B are suitable for use in optical recording media. The phthalocyanine dyes can be used in laser addressed optical recording media and describes how active layers may be deposited (Kuder, J. of Imaging Science. 1988, 32:51–56).

Phthalocyanine derivatives have also been used in Langmuir Blodgett (LB) films (UK Patent 2,229,190 B).

The redox behavior of phthalocyanines is also of interest. Some uses which exploit the redox properties of phthalocyanines include electrocatalysis, photocatalysis, photovoltaics, electric conduction, photoconductivity and electrochromism (A.B.P. Lever, Chemtech, 1987, 17:506–510). It may be desirable to be able to exert control over the redox properties of phthalocyanine type compounds (Milaeva et al, *Doklady Akademic Nauk, SSSR* 1989, 306:1387–90). For example, the redox properties of phthalocyanines such as dodecachloro-tetra (3,5-di-tert-butyl-4-hydroxy phenyl) phthalocyanine have been studied by other researchers.

A further aspect of the invention includes use of the compounds of the invention, in a liquid crystal device. Typically such devices include linear and non-linear electrical, optical and electro-optical devices, magneto-optical devices, and devices providing responses to stimuli such as temperature changes and total or partial pressure changes.

Polyethylene oxides can complex alkali metal ions, for example Li and have been used as polyelectrolytes in solid state battery applications (Charadame, *Macromolecules* ed. Benoit and Rempp, (Pergamon Press:New York, 1982), 226). The compounds of the invention may also be useful as polyelectrolytes, they are able to stabilize charge, therefore there exist a number of applications within battery technology.

The compounds of the present invention are suitable for use in optical recording media. Typically the phthalocyanine will absorb in the near-infrared. In order to make an optical recording media using a near-infrared absorber, the near-infrared absorber may be coated or vacuum-deposited onto a transparent substrate (EP 0 337 209 A2)., Display materials can be made by mixing a near-infrared absorber of formula I with liquid crystal materials such as nematic liquid crystals, smectic liquid crystals and cholesteric liquid crystals (EP 0 337 209 A2). The compounds of the current invention may be incorporated into liquid crystal panels wherein the near-infrared absorber is incorporated with the liquid crystal and laser beam is used to write an image. Mixtures of phthalocyanines of the current invention may be mixed with liquid crystal materials in order to be used in guest-host systems. Furthermore, phthalocyanines compounds can be incorporated into liquid crystal materials and subsequently used in electrooptical devices (GB 2,229,190 B).

It may be advantageous to polymerize certain of the compounds described by the current invention. Polymerized phthalocyanines may be used in, for example, LB films. There are numerous ways by which the phthalocyanine compound may be polymerized. Polymerization may be effected via the central metal atom or metal compound, or polymerization may be realized by another method known in the art. An example of a suitable phthalocyanine substituent which may be used to effect polymerization is an unsaturated substituent such as an alkene group.

Main chain or side chain liquid crystal polymers may also be made using the compounds of the present invention, or metal-metal linked liquid crystal polymers. LB films including compounds of the current invention may be used as optical or thermally addressable storage media. The compounds of the current invention may also be used as molecular wires (R.J.M. Nolte et al. *Angew. Chem. Int. Ed. Eng.*, 1994, 33(21):2173).

It is known that some phthalocyanines are excellent generators of third order non-linear optical effects and thus show promise for use in photonic devices including all-optical switches and computers (Bredas et al. *Chem. Rev.* 1994, 94:243). The materials of the present invention may show such effects and be used in such devices.

The compounds of the present invention allow for electronic interaction of substituents with the phthalocyanine ring. The redox properties of the phthalocyanines described by the current invention may be easily modified by the introduction of phenolic substituents. The compounds described by the current invention are useful, for example, in the following: electrocatalysis, photocatalysis, photovoltaics, electric conduction, photoconductivity and electrochromism and other applications which exploit redox properties.

EXEMPLIFICATION OF THE INVENTION

The invention is further illustrated by the following examples which should not be construed as limiting.

EXAMPLE 1

Synthesis of Fluorinated Phthalonitriles

Phthalonitriles are known precursor to phthalocyanines. Although many phthalonitriles are known, among the perfluorinated ones only the parent, 1,2-dicyano3,4,5,6-tetrafluorobenzene (TFP) is known (D. Britton, *Acta Crystallogr. Sect. C (CrStr. Comm.)* 44:1020 (1988)) despite the fact that 'isogeometric' replacement of C—H by strong C—F bonds (107 kcal/mol) is expected to impart enhanced thermal stability, lipophilicity and chemical inertness (R. Krishnamurti, et al., *J. Org. Chem.* 56:984 (1994); M. R. C. Gerstenberger, et al. *Angew. Chem. Int. Ed. Engl.* 20:647 (1981)).

Among perfluorinated phthalonitriles, those bearing branched substituents are expected to yield non-planar phthalonitriles and phthalocyanines exhibiting useful physical properties such as enhanced solubility and steric hindrance. The preparation and molecular level characterization of the first examples of substituted perfluorinated phthalonitriles is discussed in this example (Gorun et al. *J. Fluoro. Chem.* 91:37–40 (1998)).

The reaction of perfluoropropene (PFP) with TFP was performed. A series of products with varying degrees of substitution are readily obtained (Scheme 2, below).

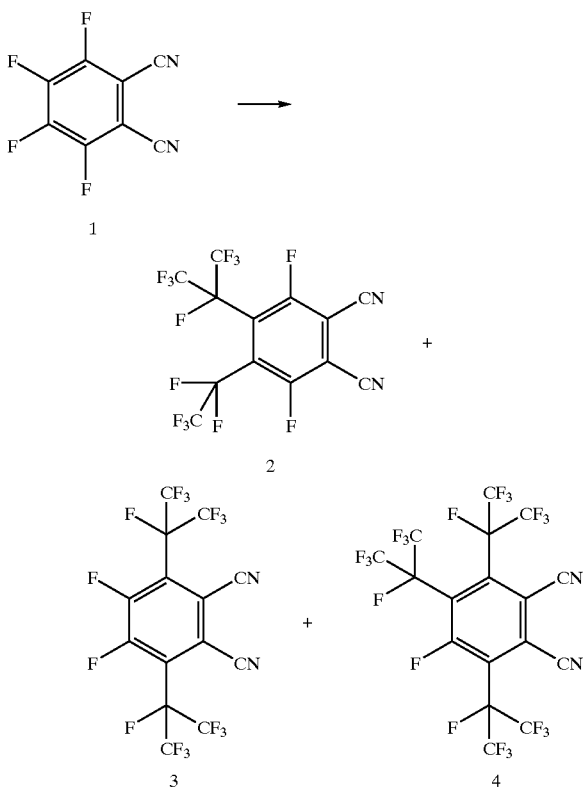

Scheme 2

Of the four possible disubstituted isomers only perfluoro-(4,5-di-isopropyl phthalonitrile), 2, (43% yield) and perfluoro-(3,6-di-isopropyl phthalonitrile), 3, (6% yield) have been observed. Only one tris-substituted isomer, 4, has been isolated (20% yield).

A comparison of the X-ray structures of 2 and 3 reveals that i-$C_3F_7$ groups adopt the minimum energy conformation, with the tertiary fluorines in 2 located approximately in the plane of the aromatic rings. This 'head-to-head' conformation (F and $CF_3$ viewed as 'head' and 'tails', respectively) forces both $CF_3$ groups above and below the aromatic ring thus maximizing the distance of the bulky $CF_3$ groups from the phthalonitrile plane. For both 2 and 3, modeling studies suggest that this conformation is favored by a minimum in the $CF_3$—$CF_3$ and CN—$CF_3$ repulsions, respectively.

Head-to-head conformations are also expected to occur in other phthalonitriles and phthalocyanines with iso-substituted haloalkanes, e.g, fluoroalkanes, because carbon chain homologation results in tail expansion above and/or below the aromatic ring.

Materials and Methods

All chemical reactions were carried out under a nitrogen atmosphere. Solvents were dried using conventional methods except for the solvents used for extraction and chromatography which were not purified. Anhydrous CsF, PFP and TFP (Aldrich) have been used without purification. Melting points were not corrected. NMR spectra have been recorded on Bruker 250 and 400 MHz instruments. FAB mass spectra have been obtained in m-nitrobenzyl alcohol (NBA)/NaI matrices using a Kratos MS80 spectrometer.

A Fischer-Porter bottle, containing 0.464 g (2.32 mmol) of TFP, 0.103 g (0.69 mmol) of anhydrous CsF and 30 ml of dry acetonitrile was cooled to −78° C. Approximately 2.5 g (16.7 mmol) of hexafluoropropene was condensed and the bottle was sealed. The cooling bath was removed and the bottle was sealed. The cooling bath was removed and the reaction was allowed to warm to room temperature. After stirring for 45 min at room temperature the reaction was vented to release unreacted hexafluoropropene, and quenched by addition to 100 ml of brine. The mixture was extracted with ethyl acetate and flash chromatographed on 40 µm silica gel using toluene/hexanes (1:5) to give 0.50 g (43%) of 2, 0.49 g (43%) of 4, and finally 0.07 g (6%) of 3 (order of elution).

2: mp 101–101.5° C., $^{19}$F NMR ($d_6$-acetone, $CFCl_3$ std, J in Hz) d: −71.1 (dt, J 32.2, 6.4), −93.7 (md, J=6.4), −165.43 (m). $^{13}$C NMR ($d_6$-acetone) d: 158.6, 123.7, 120.5, 112.8, 109.0, 94.1. MS: 523 (2+ Na$^+$), 500 (2), 431 (2—$CF_3$).

3: mp 122.5–123° C., $^{19}$F NMR ($d_6$-acetone, $CFCl_3$ std, J in Hz) d −73.2 (dd, J=22.5, 6.4), −114.3 (m), −171.1 (m). $^{13}$C NMR ($d_6$-acetone) d: 152.3, 123.5, 120.1, 118.1, 112.2, 92.0. MS: 676 (3+ NBA +Na$^+$), 523 (3+ Na$^+$).

4: mp 89.5–90° C., $^3$C NMR ($d_6$-acetone, $CFCl_3$ STD, J IN Hz) d −68.0 (d, J=32.1), −73.2 (dd, J=25.7, 6.4), −138.6 (s), −170.3 (m), −171.6 (m, J=51.4–54.6). $^{13}$C NMR ($d_6$-acetone) d: 158.7, 138.3, 127.5, 124.0, 123.9, 123.1,120.8, 120.6, 120.5, 113.5, 112.6, 96.6, 95.6, 92.7. MS: 826 (4+ NBA+ Na$^+$), 673 (4+ Na$^+$).

EXAMPLE 2

Synthesis of Zinc Octakis (perfluoroisopropyl) Perfluorophthalocyanine, Bis-acetone Solvate ("ZnPcF64")

In Examples 2–6, $^{19}$F NMR spectra reveal the correct ratios for aromatic and aliphatic fluorines for all the compounds. The chemical shifts are reported in ppm. vs. $CFCl_3$. X-ray diffraction studies were performed at low temperature. All compounds exhibit characteristic Sorret and Q bands in their UV-Vis spectra.

Method 1

1.363 g (2.725 mmol) of 1,2 cyano-3,6-fluoro-4,5-perfluoroisopropyl-benzene (2) and 0.500 g (2.725 mmol) of solid zinc acetate were heated to 220° C. for four hours in 1-chloronaphthanlene. The colorless mixture turned deep green blue after two hours. After removing the solvent, the resulting crude material was purified by column chromatography using acetone/hexanes mixtures.

Method 2

1.191 g (2.381 mmol) of 1,2 cyano-3,6-fluoro-4,5-perfluoroisopropyl-benzene (2) and 0.109 g (.5953 mmole) of solid zinc acetate were heated at 270° C. in a closed vessel for 2.5 hours. The reaction was cooled and the crude material was purified by column chromatography using acetone/hexanes mixtures.

Figure 2:
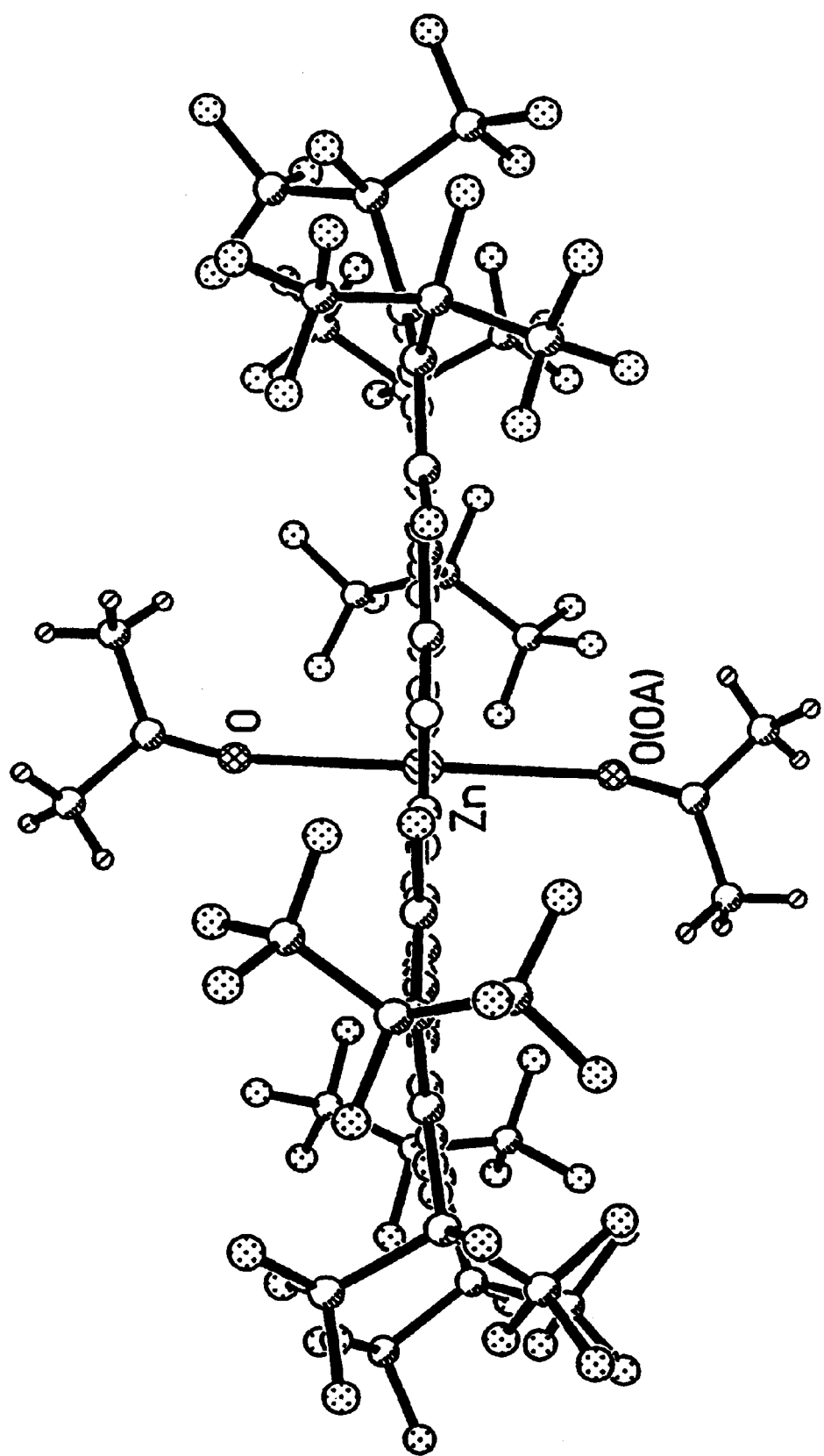
FIG. 2 is a side view of the molecule shown in FIG. 1, showing the two acetone ligands as well. Carbonyl oxygens (O and O(OA)) are represented by diamond circles, and the methyl hydrogen atoms of the acetone ligands are represented by the smallest circles.

The structure of zinc octakis (perfluoroisopropyl) perfluorophthalocyanine, bis-acetone solvate was determined by X-ray crystallography and is shown in FIG. 1. The X-ray structure demonstrates the presence of the Zn ion in the center of the phthalocyanine ring, which is substituted at its periphery by fluoro and perfluoro isopropyl groups. FIG. 2 shows the two acetone molecules bonded to the zinc ion, rendering the composition of the complex $Zn^1L_1$ (acetone)$_2$.

$^{19}$F NMR: −164 (aromatic F); −71.3 (CF$_3$); and −105.4 (tertiary F). The molecular weight of the compound was confirmed by mass spectrometry.

EXAMPLE 3

Synthesis of Ruthenium Octakis (Perfluoroisopropyl) Perfluorophthalocyanine, Carbon Monoxide Method 1

1.0073 g (2.014 mmol) of 1,2 cyano-3,6-fluoro-4,5-perfluoroisopropyl-benzene (2) and 0.1024 g (0.156 mmol) of triruthenium dodecacarbonyl in 10 mL of 1-chloronapthalene was refluxed with for 24 hours at 280° C. under an argon atmosphere. The dark greenish blue solution was cooled to room temperature and then poured into 200 mL of degassed hexane. The precipitate was filtered and the solvent was removed in vacuum. The crude material was sublimed then purified by Soxhlet extraction with hexanes and acetone. The purified material was dried at 150° C. under vacuum for 12 hours giving a dark blue powder.

Method 2

1.0243 g (2.05 mmol) of 1,2 cyano-3,6-fluoro-4,5-perfluoroisopropyl-benzene (2) and 1.066 g (0.167 mmol) of triruthenium dodecacarbonyl were heated at 270° C. in a closed vessel for four hours and cooled to room temperature. The crude product was sublimed at 150° C. under vacuum for 12 hours to remove unreacted starting material. It was then purified by Soxhlet extraction with pentane and acetone. The purified material was dried at 150° C. under vacuum for 12 hours.

$^{19}$F NMR: −154.7 (aromatic F); −71.4 (CF$_3$); and −94.6 (tertiary F). $v_{co}$=2021 cm$^{-1}$.

Figure 3:
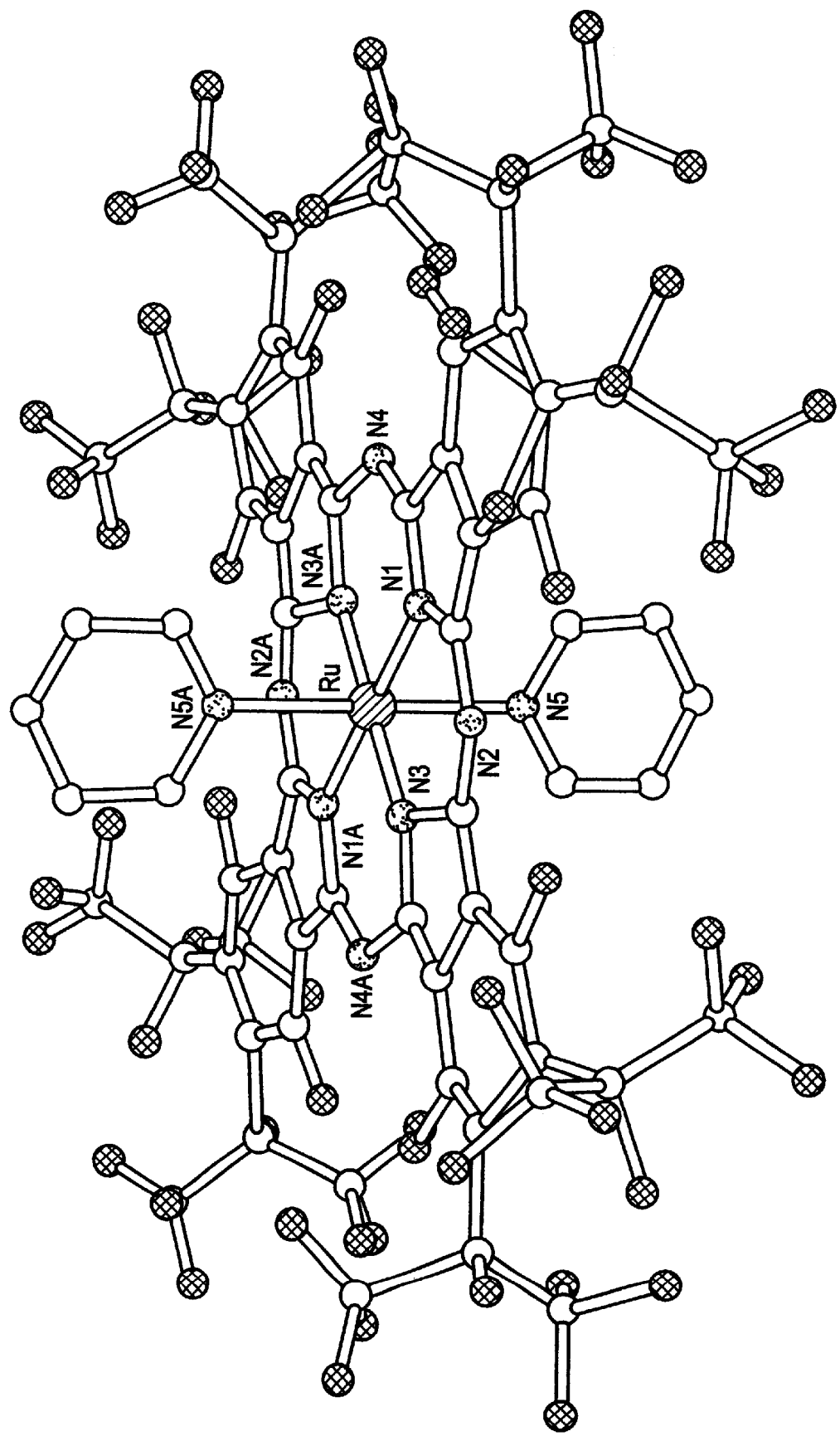
FIG. 3 is a perspective view of the single crystal X-ray structure of ruthenium octakis (perfluoroisopropyl) perfluorophthalocyanine bis-pyridine. Only the ruthenium and nitrogen atoms are labeled. Atoms labeled N5 and N5A are the nitrogen atoms in the two pyridine rings, respectively.

Recrystallization from pyridine yields the bis-dipyridine solvate. $^{19}$F NMR: −164.8 (aromatic F); −71.4 (CF$_3$); and −106.0 (tertiary F). The molecular weight was confirmed by mass spectrometry. The structure of ruthenium octakis (perfluoroisopropyl) perfluorophthalocyanine bis-pyridine was determined by X-ray crystallography and is shown in FIG. 3.

EXAMPLE 4

Synthesis of Manganese Octakis (Perfluoroisopropyl) Perfluorophthalocyanine 1,2 cyano-3,6-fluoro-4,5-perfluoroisopropyl-benzene (2) and anhydrous manganese (II) acetate were heated to 220° C. for four hours in 1-chloronaphthalene. After removing the solvent, the resulting crude material was purified by fractional crystallization from ethyl acetate/ethyl ether.

$^{19}$F NMR: −158.4 (aromatic F); −71.0 (CF$_3$); and −105.4 (tertiary F). The molecular weight was confirmed by mass spectrometry.

EXAMPLE 5

Synthesis of Cobalt Octakis (Perfluoroisopropyl) Perfluorophthalocyanine, Bis Methanol Solvate 1,2 cyano-3,6-fluoro-4,5-perfluoroisopropyl-benzene.(2) and cobalt (II) acetate were heated to 220° C. for four hours in 1-chloronaphthalene. After removing the solvent, the resulting crude material was purified by fractional crystallization from methanol.

$^{19}$F NMR: −164.6 (aromatic F); −71.2 (CF$_3$); and −104.0 (tertiary F). The molecular weight was confirmed by mass spectrometry. The composition of the cobalt complex, as determined via single-crystal X-ray diffraction, indicates the presence of two solvated methanol molecules. The mass spectrum shows the desolvated molecular ion.

EXAMPLE 6

Synthesis of Iron Octakis (Perfluoroisopropyl) Perfluorophthalocyanine 1,2 cyano-3,6-fluoro-4,5-periluoroisopropyl-benzene (2) and iron pentacarbonyl in 10 mL of 1-chloronapthalene was refluxed with stirring for 24 hours at 280° C. under an argon atmosphere. The solution was cooled to room temperature and then poured into 200 mL of degassed hexane. The precipitate was filtered and the solvent was removed in vacuum. The crude material was sublimed then purified by Soxhlet extraction with hexanes and acetone. The purified material was dried at 150° C. under vacuum. (Iron octakis (perfluoroisopropyl) perfluorophthalocyanine can also be prepared using, for example, Fe$_2$(CO)$_{10}$.)

$^{19}$F NMR: −164.8 (aromatic F); −71.7 (CF$_3$); and −105 (tertiary F). The molecular weight was confirmed by mass spectrometry.

EXAMPLE 7

In vitro Phototoxicity Effects of ZnPcF$_{64}$ on Mouse Tumor Cells

Chremophor emulsions were prepared and cell photo inactivation was determined by J. E. van Lier and colleagues at the University of Sherbrooke, Sherbrooke, QC, Canada, in accordance with published procedures. (Alleman et al. *Int. J. Cancer*, 72:289–294 (1997))

Preparation of Chreinophor Emulsions:

Chremophor EL (CRM) was obtained from BASF (Toronto, Canada). All solvents were of analytical grade, and all other chemicals were commercially available products. Zinc octakis (perfluoroisopropyl) perfluorophthalocyanine ("ZnPcF$_{64}$", 2.5 mg) was first dissolved in methanol (2 mL). 500 μL of Chremophor and 150 μL of propane diol were added to the solution. The methanol was evaporated by rotory evaporation at room temperature. The residue was diluted with PBS to 5 mL and sterile filtered (0.2 μm). After dilution with 50 μL of THF, the final concentration of ZnPcF$_{64}$ was estimated to be 140 μm, based on optical density at 690 nm (Alleman et al. *Int. J. Cancer*, 72:289–294 (1997)).

Cell Photo-inactivation

EMT-6 mouse mammary tumor cells were maintained in Waymouth's medium supplemented with 15% FBS and 1% L-glutamin.(GIBCO, Burlington, Canada), according to an established protocol (Rockwell et al. J. Nat. Cancer Inst., 49:735–749 (1972); Brasseur et al. *J. Med Chem.* 37:415–420 (1994). Cell survival was estimated as previously described by means of the calorimetric 3-(4-5-dimethylthiazol-2-yl)diphenyl-tetrazolium bromide (MTT) assay (Tada et al *J. Immunol. Methods*, 93:157–165 (1986); Margaron et al. *Anticancer Res.* 63:217–223 (1996)). Briefly, 15 times 10$^3$ EMT-6 cells per well were inoculated in 100 μL Waymouth's growth medium in 96 multi-well plates and incubated overnight at 37° C. and 5% $CO_2$. Cells were rinsed twice with PBS and incubated for 1 or 24 hours at 37° C. with 100 μL of $ZnPcF_{64}$ prepared from the CRM stock solution at 1 and 3 μM in Waymouth 1% FBS.

After incubation, cells were rinsed twice with PBS, refed with 100 μl Waymouth 15% FBS and exposed to red light. The light source consisted of 2 500 W tungsten/halogen lamps (GTE Sylvania, Montreal, Canada) fitted with a circulating, refrigerated, aqueous Rhodamine filter. The fluence rate calculated over the absorbance peaks of the dyes (660–700 nm) was 10 mW $cm^{-2}$, for a total fluence of 0.6–36 $J/cm^2$. Cells were incubated at 37° C. overnight before assessing cell viability. Fifty microliters of a 5-fold diluted MTT stock solution (5 mg/ml PBS) in Waymouth 15% FBS were added to each well. After 3 hr, 100 μl SDS (10% in 0.01 N HCl) were added in the wells. Plates were incubated overnight at 37° C., after which the absorbance was read at 595 nm by means of a microplate reader (BioRad, Mississauga, Canada). The average absorbance of the blank wells in which cells were omitted was subtracted from the readings of the other wells. The average absorbance of the control cells, which were incubated with dye-free Waymouth 1% FBS, represents 100% cell survival. The light dose required to inactivate 90% of the cells ($LD_{90}$) at a given drug dose was extrapolated from the survival curves. Eight-fold replicates were run per drug and light dose, and each experiment was repeated at least 3 times.

Results

No phototoxic effects were observed under any conditions. Cell survival was 100% at the highest dye concentrations and under the longest light exposure.

EXAMPLE 8

In vivo Phototoxicity Effects of $ZnPcF_{64}$ on Mouse Tumors

The in vivo phototoxicity effects of $ZnPcF_{64}$ on mouse tumors were determined by J. E. van Lier and colleagues at the University of Sherbrooke, Sherbrooke, QC, Canada, in accordance with published procedures. (Alleman et al. Int. J. Cancer, 72:289–294 (1997))

Experimental Animals

Experiments were performed on male BALB/c mice (16–22 g) and female Fisher CDF (F-344) rats (approx. 150 g) (Charles River, Montreal, Canada) following a protocol approved by the Canadian Council on Animal Care and an in-house ethics committee. Animals were allowed free access to water and food throughout the course of the experiments. Before tumor implantation, hair on the hind legs and back of the mice was removed by shaving and chemical depilating (Nair®, Whitehall, Mississauga, Canada). A tumor was implanted on each hind thigh by intradermal injection of 2 times $10^5$ EMT-6 cells suspended in 0.05 ml Waymouth's growth medium. Biodistribution and photodynamic activity of $ZnPcF_{64}$ were assayed using a murine EMT-6 tumor model (Allémann et al. Int. J. Cancer, 72:289–294 (1997)).

Biodistribution

Mice were used 10 or 11 days after cell inoculation, when the tumor diameter and thickness reached 4–8 mm and 2–4 mm, respectively. Tumor-bearing mice were injected i.v. via the caudal vein with 1 μmol $kg^{-1}$ of dye formulated as a CRM emulsion (0.2 ml). At different time intervals after dye administration (from 3 hr to 1 week), blood was collected from the axillary vessels in the angle of the forelimb by means of heparinised syringes, after which the animals (n=5 per time interval) were killed. One milliliter of water was added to blood samples (100 mg) to induce hemolysis. Samples were then frozen (–40° C.), freeze-dried during 48 hr to dehydrate the material completely, sonicated with 3.0 ml of N,N-dimethylformamide (DMF) and incubated overnight at 37° C. with mechanical agitation. After centrifugation (2,800 g for 20 min), supernatants were sampled and further centrifuged under the same conditions. The dye concentration in the clear supernatant was assayed by fluorescence (fluorescence spectrophotometer F-2000; Hitachi, Tokyo, Japan) ($\lambda_{ex}$ 666 nm, $\lambda_{em}$ 680 nm, 5-nm band pass).

Organs and tissues of interest were removed, washed with saline (0.9%) and blotted dry. Whole tumors (40–80 mg) and aliquots of other organs (80–150 mg) were homogenized with 2.0 ml of DMF using a Polytron fitted with a PT 10/35 rotor (Beckman, Mississauga, Canada). Samples were incubated and centrifuged in the same manner as blood samples. Calibration curves were established by adding known amounts of dye to 80–150 mg of tissue samples from control mice, which tissues were treated as described above. No fluorescence was found in control tissue samples to which no dye had been added.

Photodynamic therapy

For PDT studies, mice were used 6–8 days after tumor inoculation (tumor size: 3–5 mm diameter, 2–3 mm thickness). At this time point, the tumor is sufficiently large to be measured, while therapeutic response can be observed without interference of spontaneous necrosis (Margaron et al. Anticancer Res. 16:613–620 (1996)). Animals were given an i.v. injection of $ZnPcF_{64}$ formulated as a CRM emulsion at I or 2.5 μmol $kg^{-1}$ (0.2 ml), and one tumor was treated with red light 24–72 hr later, while the other tumor served as a control. Tumors were illuminated with an 8-mm diameter beam of 650–700 nm light (100 or 200 mW . $cm^2$ for a total fluence of 100–400 J .$cm^{-2}$) generated by a 1,000 W Xenon lamp, equipped with a 10-cm circulating water filter and 2 glass filters (Corion LL650 and LS700, Holliston, Mass.). A positive tumor response (necrosis) was assigned to tumors which appeared macroscopically as flat and necrotic tissues within a few days after PDT (Allémann et al. Int. J Canc. 66:821–824 (1996)). A complete tumor regression is defined as the absence of a palpable tumor at 3 weeks after PDT. Tumor-free rats (n=3) were illuminated as described above on the back just above the right leg. and observed for 2 weeks post-PDT.

Results

After having been treated with a dose of 2.5 μmol/kg of $ZnPcF_{64}$, the mice died of shock. When the dose was lowered to 1 μmol/kg, complete tumor necrosis was found with some inflammation.

Incorporation by Reference

The entire contents of all patents, published patent applications and other references cited herein are hereby expressly incorporated herein by reference Equivalents Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A phthalocyanine compound of formula I:

$$[M_xL_yS_z]C_w \qquad (I)$$

wherein:

M is a metal;

L is an anion of a phthalocyanine compound of formula II:

(II)

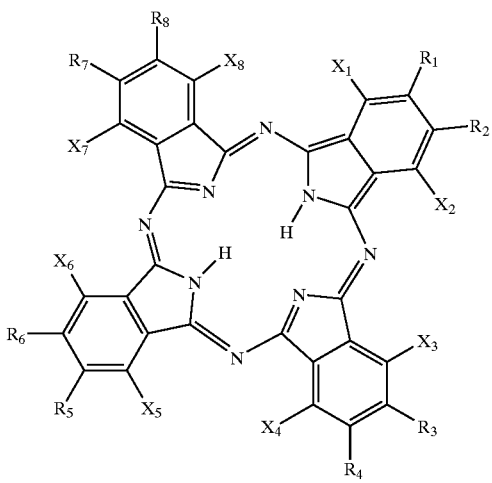

wherein:
X$_{1-8}$ are each halogen; and
R$_{1-8}$ are each independently halogen or a perhalogenated anti-stacking moiety, provided that R$_{1-8}$ are not all halogen;
S is an organic or inorganic ligand;
C is a counterion;
x and y are each one; and
z and w are numbers zero or greater, selected such that said phthalocyanine compound is electrically neutral.

2. The phthalocyanine compound of claim 1, wherein at least one of X$_{1-8}$ is fluorine.

3. The phthalocyanine compound of claim 1, wherein each of X$_{1-8}$ is fluorine.

4. The phthalocyanine compound of claim 1, wherein said anti-stacking moiety is alkyl, alkenyl, alkynyl, aryl, aralkyl or heteroaryl.

5. The phthalocyanine compound of claim 4, wherein said anti-stacking moiety is selected such that said compound is soluble in water.

6. The phthalocyanine compound of claim 4, wherein said anti-stacking moiety is substituted with at least one fluorine atom.

7. The phthalocyanine compound of claim 6, wherein said anti-stacking moiety is perfluorinated.

8. The phthalocyanine compound of claim 4, wherein said anti-stacking moiety is branched alkyl.

9. The phthalocyanine compound of claim 4, wherein said anti-stacking moiety is perhalogenated alkyl.

10. The phthalocyanine compound of claim 9, wherein said perhalogenated alkyl is perfluorinated.

11. The phthalocyanine compound of claim 10, wherein said perfluorinated alkyl is methyl, ethyl, isopropyl, isobutyl, tert-butyl or pentyl.

12. The phthalocyanine compound of claim 11, wherein said anti-stacking moiety is perfluorinated isopropyl.

13. The phthalocyanine compound of claim 4, wherein more than one of R$_1$–R$_8$ is a perhalogenated anti-stacking moiety.

14. The phthalocyanine compound of claim 13, wherein each of R$_1$–R$_8$ is a perhalogenated anti-stacking moiety.

15. The phthalocyanine compound of claim 14, wherein each of said anti-stacking moieties is perfluorinated.

16. The phthalocyanine compound of claim 15, wherein each of said anti-stacking moieties is perfluorinated alkyl.

17. The phthalocyanine compound of claim 14, wherein each of said anti-stacking moieties is perfluorinated isopropyl.

18. The phthalocyanine compound of claim 1, wherein said metal is a transition metal, metalloid, or a cation thereof.

19. The phthalocyanine compound of claim 18, wherein said metal is selected from the group consisting of Al, Si, Sc, Ti, V, Cr, Mn, Fe, Co, Ni, Cu, Zn, Ga, Ge, As, Se, and their respective ions.

20. The phthalocyanine compound of claim 18, wherein said metal is selected from the group consisting of Y, Zr, Nb, Mo, Tc, Ru, Rh, Pd, Ag, Cd, In, Sn, Sb, Te, and their respective ions.

21. The phthalocyanine compound of claim 18, wherein said metal is selected from the group consisting of La, Hf, Ta, W, Re, Os, Ir, Pt, Au, Hg, Tl, Pb, Bi, Po, and their respective ions.

22. The phthalocyanine compound of claim 19, wherein said metal is Al.

23. The phthalocyanine compound of claim 19, wherein said metal is Si.

24. The phthalocyanine compound of claim 19, wherein said metal is Mn.

25. The phthalocyanine compound of claim 19, wherein said metal is Fe.

26. The phthalocyanine compound of claim 19, wherein said metal is Co.

27. The phthalocyanine compound of claim 19, wherein said metal is Zn.

28. The phthalocyanine compound of claim 20, wherein said metal is Ru.

29. The phthalocyanine compound of claim 20, wherein said metal is Cd.

30. The phthalocyanine compound of claim 18, wherein said metal is diamagnetic.

31. The phthalocyanine compound of claim 1, wherein z is greater than zero.

32. The phthalocyanine compound of claim 31, wherein C and w are selected such that the phthalocyanine compound is neutral.

33. The phthalocyanine compound of claim 31, wherein C is anionic.

34. The phthalocyanine compound of claim 33, wherein C is selected from the group consisting of F$^-$, Br$^-$, Cl$^-$, I$^-$, NO$_3^-$, BF$_4^-$, OH$^-$, PF$_6^-$, SO$_4^{2-}$, ClO$_4^-$, CO$_2$H$^-$, SO$_3$H$^-$, and carbon based anions.

35. The phthalocyanine compound of claim 31, wherein C is an organic or organometallic cation.

36. The phthalocyanine compound of claim 35, wherein C is selected from the group consisting of PR$_4^+$, NR$_4^+$, and AsR$_4^+$, wherein R is alkyl, aryl, or aralkyl.

37. The phthalocyanine compound of claim 1, wherein S is selected from the group consisting of acetone, methanol, ethanol, propanol, carbon monoxide, pyridine, carbon dioxide, sulfur dioxide, and halogenated hydrocarbons.

38. The phthalocyanine compound of claim 1, wherein said phthalocyanine compound is zinc octakis (perfluoroisopropyl) perfluorophthalocyanine, ruthenium octakis(perfluoroisopropyl) perfluorophthalocyanine, manganese octakis(perfluoroisopropyl) perfluorophthalocyanine, iron octakis(perfluoroisopropyl) perfluorophthalocyanine, or cobalt octakis (perfluoroisopropyl) perfluorophthalocyanine.

39. The phthalocyanine compound of claim 1, wherein M is a cation.

40. A phthalocyanine compound of formula I:

    I wherein:

M is a metal;

L is an anion of a phthalocyanine compound of formula II

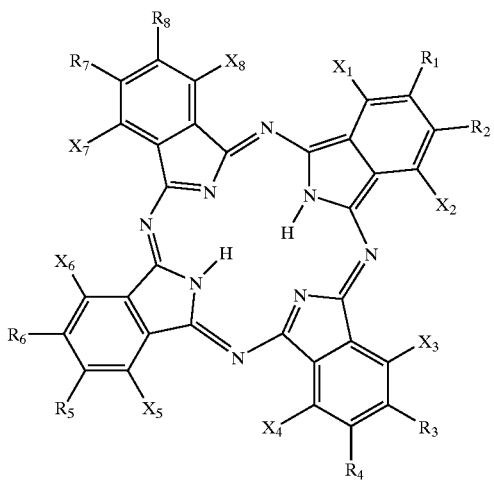

wherein:

$X_{1-8}$ are each halogen; and $R_{1-8}$ are each independently halogen or a perhalogenated anti-stacking moiety, provided that $R_{1-8}$ are not all halogen;

S is an organic or inorganic ligand;

C is a counterion;

x and y are each one; and z and w are numbers zero or greater, selected such that said phthalocyanine compound is electrically neutral;

said compound having been prepared by a process comprising heating a phthalonitrile and a metal under conditions such that said compound is formed.

41. The phthalocyanine compound of claim 1 or 40, wherein said compound is a substantially pure isomer.

42. A pharmaceutical composition, comprising a pharmaceutically acceptable carrier and an effective amount of a phthalocyanine compound of formula I:

    I wherein:

M is a metal;

L is an anion of a phthalocyanine compound of formula II

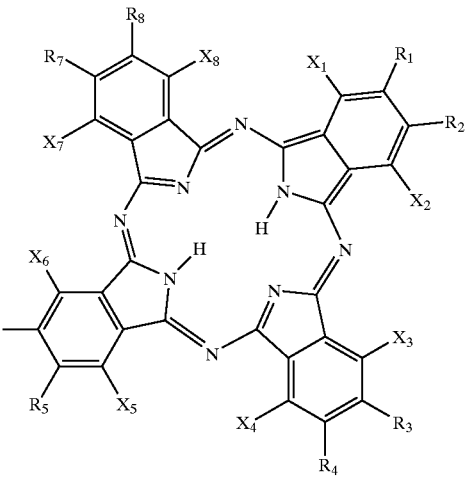

wherein:

$X_{1-8}$ are each halogen; and $R_{1-8}$ are each independently halogen or a perhalogenated anti-stacking moiety, provided that $R_{1-8}$ are not all halogen;

S is an organic or inorganic ligand;

C is a counterion;

x and y are each one; and z and w are numbers zero or greater, selected such that said phthalocyanine compound is electrically neutral, and pharmaceutically acceptable salts thereof.

43. The pharmaceutical composition of claim 42, wherein said effective amount is effective for photodynamic therapy.

44. The pharmaceutical composition of claim 42, wherein said effective amount is effective for treatment of cancer, wherein said cancer is selected from the group consisting of metastatic breast cancer, endometrial carcinoma, bladder cancer, malignant melanoma, Kaposi's sarcoma, basal cell carcinoma, chondrosarcoma, squamous cell carcinoma, prostate carcinoma, laryngeal papilloma, mycosis fungoides, superficial cancer of the tracheobronchial tree, cutaneous/mucosal papilloma, gastric cancer, and enteric cancer.

45. The pharmaceutical composition of claim 42, wherein each of $X_{1-8}$ is fluorine.

46. The pharmaceutical composition of claim 42, wherein said perhalogenated anti-stacking moiety is selected from the group consisting of alkyl, alkenyl, alkynyl, aryl, aralkyl or heteroaryl.

47. The pharmaceutical composition of claim 46, wherein said anti-stacking moiety is perfluorinated.

48. The pharmaceutical composition of claim 42, wherein each of $R_1$–$R_8$ is a perhalogenated anti-stacking moiety.

49. The pharmaceutical composition of claim 48, wherein each of said anti-stacking moieties is perfluorinated.

50. The pharmaceutical composition of claim 49, wherein each of said anti-stacking moieties is alkyl.

51. The pharmaceutical composition of claim 42, wherein M is a diamagnetic metal cation.

52. The pharmaceutical composition of claim 51, wherein M is Al, Si, Mn, Fe, Co, Zn, Ru, or Cd.

53. The pharmaceutical composition of claim 42, wherein said phthalocyanine compound is zinc octakis (perfluoroisopropyl) perfluorophthalocyanine, ruthenium octakis(perfluoroisopropyl) perfluorophthalocyanine, manganese octakis(perfluoroisopropyl) perfluorophthalocyanine, or cobalt octakis(perfluoroisopropyl) perfluorophthalocyanine.

54. A phthalocyanines compound of formula (1):

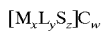  (I)

wherein:

M is a metal;

L is an anion of a phthalocyanine compound of formula II:

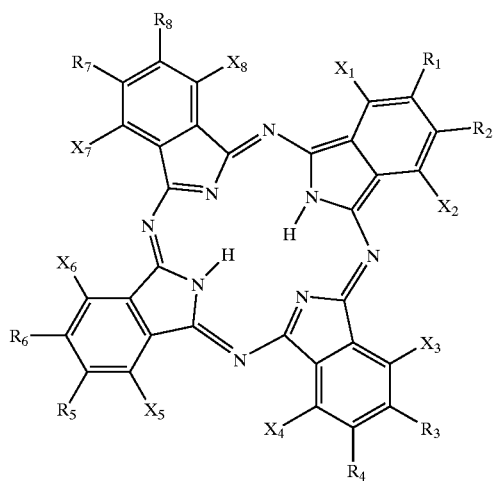 (II)

wherein:

$X_{1-8}$ are each halogen; and $R_{1-8}$ are each independently halogen or a perhalogenated alkyl, provided that $R_{1-8}$ are not all halogen;

S is an organic or inorganic ligand, selected from group consisting of acetone, pyridine, methanol, DMF, THF, water, ethanol, propanol, CO, $CO_2$ and $SO_2$;

C is a counterion;

x and y are each independently one or two, z is zero, one or two; and w is zero.

55. The phthalocyanine compound of claim 54, wherein at least one of $X_{1-8}$ is fluorine.

56. The phthalocyanine compound of claim 55, wherein each of $X_{1-8}$ is fluorine.

57. The phthalocyanine compound of claim 54, wherein said at least one of $R_1-R_8$ are perhalogenated alkyl.

58. The phthalocyanine compound of claim 57, wherein said perhalogenated alkyl is perfluorinated.

59. The phthalocyanine compound of claim 58, wherein said perfluorinated alkyl is methyl, ethyl, isopropyl, isobutyl, tert-butyl or pentyl.

60. The phthalocyanine compound of claim 59, wherein said perfluorinated alkyl is perfluorinated isopropyl.

61. The phthalocyanine compound of claim 57, wherein each of $R_1-R_8$ is perhalogenated alkyl.

62. The phthalocyanine compound of claim 61, wherein each of $R_1-R_8$ is perfluorinated.

63. The phthalocyanine compound of claim 62, wherein each of $R_1-R_8$ is perfluorinated isopropyl.

64. The phthalocyanine compound of claim 54, wherein said metal is a transition metal, metalloid, or a cation thereof.

65. The phthalocyanine compound of claim 64, wherein said metal is selected from the group consisting of Al, Si, Sc, Ti, V, Cr, Mn, Fe, Co, Ni, Cu, Zn, Ga, Ce, As, Se, and their reactive ions.

66. The phthalocyanine compound of claim 64, wherein said metal is selected from the group consisting of Y, Zr, Nb, Mo, Tc, Ru, Rh, Pd, Ag, Cd, In, Su, Sb, Te, and their respective ions.

67. The phthalocyanine compound of claim 64, wherein said metal is selected from the group consisting of La, Hf, Ta, W, Re, Os, Ir, Pt, Au, Hg, Tl, Pb, Bi, Po, and their respective ions.

68. The phthalocyanine compound of claim 64, wherein said metal is diamagnetic.

69. The phthalocyanine compound of claim 54, wherein z is greater than zero.

70. A pharmaceutical composition, comprising an effective amount of a phthalocyanine compound of claim 54, and pharmaceutically acceptable salts thereof, and a pharmaceutically acceptable carrier.

* * * * *